United States Patent
Hariri et al.

(10) Patent No.: US 10,434,005 B2
(45) Date of Patent: *Oct. 8, 2019

(54) APPARATUSES AND METHODS FOR DISRUPTING AND PREVENTING SNORE

(71) Applicants: Aliasghar Hariri, North York (CA); Sahar Hariri, Toronto (CA)

(72) Inventors: Aliasghar Hariri, North York (CA); Sahar Hariri, Toronto (CA)

(*) Notice: Subject to any disclaimer, the term of this patent is extended or adjusted under 35 U.S.C. 154(b) by 532 days.

This patent is subject to a terminal disclaimer.

(21) Appl. No.: 15/067,824

(22) Filed: Mar. 11, 2016

(65) Prior Publication Data
US 2016/0270948 A1 Sep. 22, 2016

Related U.S. Application Data

(60) Provisional application No. 62/294,670, filed on Feb. 12, 2016, provisional application No. 62/133,958, filed on Mar. 16, 2015.

(30) Foreign Application Priority Data

Jul. 7, 2015 (WO) ................ PCT/CA2015/050630

(51) Int. Cl.
*A61B 5/00* (2006.01)
*A61H 9/00* (2006.01)
(Continued)

(52) U.S. Cl.
CPC .............. *A61F 5/56* (2013.01); *A61B 5/4818* (2013.01); *A61H 9/0078* (2013.01);
(Continued)

(58) Field of Classification Search
CPC .......... A61H 7/001; A61H 9/00; A61H 9/005; A61H 9/0078; A61H 2201/0134;
(Continued)

(56) References Cited

U.S. PATENT DOCUMENTS

| | | | |
|---|---|---|---|
| 2,235,138 A | 3/1941 | Billetter | |
| 3,723,027 A | 3/1973 | Montelius | |

(Continued)

FOREIGN PATENT DOCUMENTS

| | | |
|---|---|---|
| CN | 203634352 U | 6/2014 |
| CN | 204889426 U | 12/2015 |
| JP | 2006051223 A | 2/2006 |

OTHER PUBLICATIONS

WIPO, International Search Report and Written Opinion for PCT Application No. PCT/CA2016/000066 dated Jun. 7, 2016.

(Continued)

*Primary Examiner* — Justine R Yu
*Assistant Examiner* — Alexander Morales
(74) *Attorney, Agent, or Firm* — Lorelei G. Graham

(57) ABSTRACT

Apparatuses and methods for disrupting or preventing snoring are provided. One apparatus includes a bladder assembly comprising a collapsible structure and an inflatable bladder positioned within the collapsible structure, a conduit connecting an air inflator to the inflatable bladder, a controller in communication with the air inflator to actuate the air inflator to inflate the inflatable bladder, and an audio processor in communication with the controller. The inflatable bladder is configured to be inflated such that an entire top surface of the collapsible structure rises simultaneously along a length of the bladder assembly while the collapsible structure supports a head of a user. The audio processor is configured to detect sound waves and transmit control commands to the controller to trigger actuation of the air inflator upon detection of a trigger event.

21 Claims, 26 Drawing Sheets

(51) Int. Cl.
*G16H 20/30* (2018.01)
*A61F 5/56* (2006.01)

(52) U.S. Cl.
CPC ..... *G16H 20/30* (2018.01); *A61H 2201/0134* (2013.01); *A61H 2201/0165* (2013.01); *A61H 2201/0169* (2013.01); *A61H 2201/1246* (2013.01); *A61H 2201/1604* (2013.01); *A61H 2201/1664* (2013.01); *A61H 2201/5007* (2013.01); *A61H 2201/5012* (2013.01); *A61H 2201/5015* (2013.01); *A61H 2201/5041* (2013.01); *A61H 2201/5048* (2013.01); *A61H 2201/5058* (2013.01); *A61H 2201/5097* (2013.01)

(58) Field of Classification Search
CPC .... A61H 2201/0169; A61H 2201/5048; A61F 5/56; A47G 9/10; A47G 9/1027; A47G 9/1081; A47C 27/08–084; A47C 27/10; A61B 5/4818; A61B 5/00
USPC ............. 128/848; 5/636, 713; 601/150, 148, 601/152; 602/902
See application file for complete search history.

(56) References Cited

U.S. PATENT DOCUMENTS

| | | | |
|---|---|---|---|
| 3,998,209 A | 12/1976 | Macvaugh | |
| 4,606,087 A * | 8/1986 | Alivizatos | A47C 27/086 190/2 |
| 4,635,620 A | 1/1987 | Ricchio | |
| 4,850,067 A | 7/1989 | Latorre | |
| 4,908,887 A | 3/1990 | Shaw, Jr. | |
| 4,941,478 A | 7/1990 | Takeuchi et al. | |
| 4,991,222 A | 2/1991 | Nixdorf | |
| 5,068,933 A | 12/1991 | Sexton | |
| 5,184,365 A | 2/1993 | Stafford | |
| 5,407,330 A | 4/1995 | Rimington | |
| 5,567,127 A | 10/1996 | Wentz | |
| 5,572,757 A | 11/1996 | O'sullivan | |
| 5,708,999 A | 1/1998 | Priolo | |
| 5,771,514 A | 6/1998 | Wilhoit | |
| 5,711,652 A | 7/1998 | Van De Venne | |
| 5,844,996 A | 12/1998 | Enzmann | |
| 5,953,777 A * | 9/1999 | Buck | A47G 9/10 5/490 |
| 6,386,201 B1 * | 5/2002 | Fard | A61F 5/56 128/848 |
| 6,951,038 B1 | 10/2005 | Ganoe | |
| 7,127,759 B2 * | 10/2006 | Koops | A47G 9/10 5/644 |
| D546,105 S * | 7/2007 | McMillian | D6/601 |
| 7,594,288 B1 | 9/2009 | Holliday | |
| 7,676,870 B2 | 3/2010 | Chen | |
| 8,176,921 B2 | 5/2012 | Bazargani | |
| 8,325,934 B2 * | 12/2012 | Kuo | A47C 21/003 381/66 |
| 8,832,887 B2 | 9/2014 | Mossbeck | |
| 9,032,570 B1 * | 5/2015 | Benami | A47G 9/1009 5/640 |
| 2004/0031492 A1 | 2/2004 | Kawamura | |
| 2004/0139549 A1 * | 7/2004 | Mohrekesh | A47G 9/10 5/636 |
| 2004/0204742 A1 * | 10/2004 | Graham | A61H 1/0218 606/240 |
| 2004/0260217 A1 | 12/2004 | Gardner | |
| 2005/0091748 A1 * | 5/2005 | Ku | A47G 9/1027 5/636 |
| 2005/0102757 A1 * | 5/2005 | Lee | A47G 9/10 5/636 |
| 2005/0172409 A1 | 8/2005 | Koops | |
| 2005/0287007 A1 | 12/2005 | Leonhard | |
| 2006/0005314 A1 | 1/2006 | Lee | |
| 2006/0150338 A1 | 7/2006 | Jackson, III | |
| 2007/0061976 A1 | 3/2007 | Bazargani | |
| 2007/0213650 A1 | 9/2007 | Raley | |
| 2008/0028529 A1 * | 2/2008 | Abell | A47G 9/0253 5/640 |
| 2008/0109965 A1 * | 5/2008 | Mossbeck | A47C 23/047 5/713 |
| 2008/0306396 A1 | 12/2008 | Ariav | |
| 2010/0224198 A1 | 9/2010 | Ayuse | |
| 2010/0313359 A1 * | 12/2010 | Scott | A47G 9/1027 5/655.3 |
| 2011/0016633 A1 * | 1/2011 | Eason | A47C 20/026 5/655.9 |
| 2011/0271964 A1 | 11/2011 | Zhang | |
| 2011/0283460 A1 * | 11/2011 | Chan | A47G 9/1027 5/713 |
| 2012/0079660 A1 | 4/2012 | Chen | |
| 2012/0222218 A1 | 9/2012 | Davis | |
| 2013/0019409 A1 * | 1/2013 | Blazar | A47G 9/1027 5/644 |
| 2014/0024986 A1 | 1/2014 | Souma | |
| 2014/0259417 A1 * | 9/2014 | Nunn | A61G 7/015 5/614 |
| 2014/0296747 A1 | 10/2014 | Herrnsdorf | |
| 2014/0303533 A1 | 10/2014 | Zeutzius | |
| 2014/0310878 A1 * | 10/2014 | Herrnsdorf | A61F 5/56 5/640 |
| 2015/0150391 A1 | 6/2015 | Hsu | |
| 2015/0190304 A1 * | 7/2015 | Lawrie | A61H 15/0092 601/118 |
| 2015/0265075 A1 | 9/2015 | Liu | |
| 2016/0066716 A1 | 3/2016 | Rao | |
| 2016/0270567 A1 * | 9/2016 | Hsu | A47G 9/1081 |
| 2017/0105867 A1 | 4/2017 | Hsieh | |
| 2017/0238736 A1 | 8/2017 | Ho | |
| 2018/0028351 A1 | 2/2018 | Chang | |

OTHER PUBLICATIONS

Espacenet, Translation of abstract for CN203634352U, retrieved on Jul. 12, 2016.
Espacenet, Translation of abstract for JP2006051223A, retrieved on Jul. 12, 2016.
Espacenet, Translation of abstract for CN204889426U, retrieved on Jul. 12, 2016.
CIPO, Office Action for CA Application No. 2,979,728 dated Oct. 16, 2017.
WIPO, International Search Report and Written Opinion for PCT Application No. PCT/CA2015/050630 dated Mar. 9, 2016.
Goggle Patent, Translation of Abstract for CN203634352, retrieved on Jun. 17, 2016.
Goggle Patent, Translation of Abstract for JP2006051223, retrieved on Jun. 17, 2016.
Anti-Snore Pillow—Back in Action at https://www.backinaction.co.uk/snore-pillow, 3 pages.
amazon.com Smart Sensor Anti-Snore Pillow at http://www.amazon.com/Atlantic-Horizon-International-Sensor-Anti-Snore/dp/B00L4KEYZW/ref=sr_1_15?s=hpc&ie=UTF8&qid=1413832282&sr=1-15&keywords=anti+snore%2C+pillow, 5 pages.
amazon.com Smart Anti-Snore Pillow at http://www.amazon.com/PMT-MEDICAL-Smart-Snore-Pillow/dp/B004SE771Y/ref=sr_1_12?s=hpc&ie=UTF8&qid=1413832282&sr=1-12&keywords=anti+snore%2C+pillow, 5 pages.
The Smart Anti-snore Pillow: Helping you and your partner sleep better at http://mysmartpillow.com, 2 pages.
Gizmodo Sleep Number's IQ Bed Can Silence a Snoring Bedmate at http://gizmodo.com/sleep-numbers-iq-bed-can-silence-a-snoring-bedmate-1497526778, 4 pages.
Patent Cooperation Treaty, Notification of Transmittal of the International Search Report and Written Opinion of the International Searching Authority for PCT/CA2015/050630, Mar. 9, 2016, 9 pages.
Translation from Google Patent of CN202740193U, 2 pages.
Translation from Google Patent of CN203634352U, 4 pages.

(56) References Cited

OTHER PUBLICATIONS

Translation from Google Patent of JP2006051223A, 14 pages.
Office Action dated Apr. 17, 2018 in CA Application No. 2,979,728.
Office Action dated Nov. 6, 2018 in CA Application No. 2,979,728.
Non-Final Office Action dated Aug. 7, 2018 in U.S. Appl. No. 15/558,266.
Non-Final Office Action dated Aug. 8, 2018 in U.S. Appl. No. 15/558,284.
Final Office Action dated Jan. 22, 2019 in U.S. Appl. No. 15/558,266.
Translation from Google Patent of CN204889426U, 8 pages.

* cited by examiner

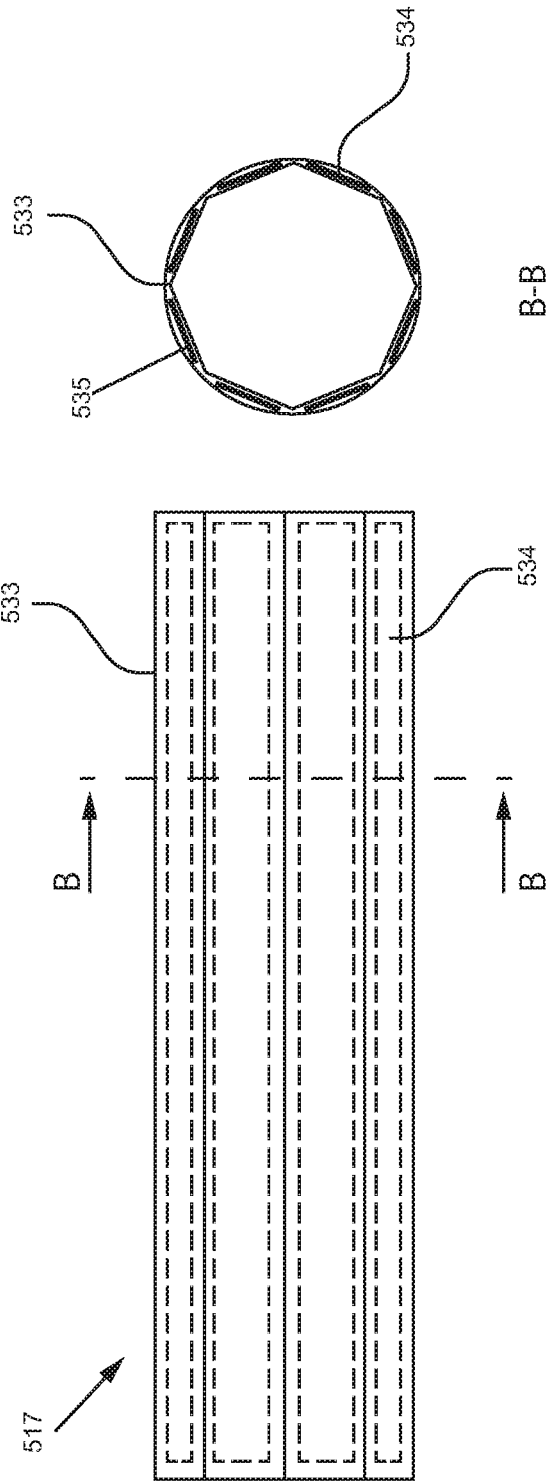

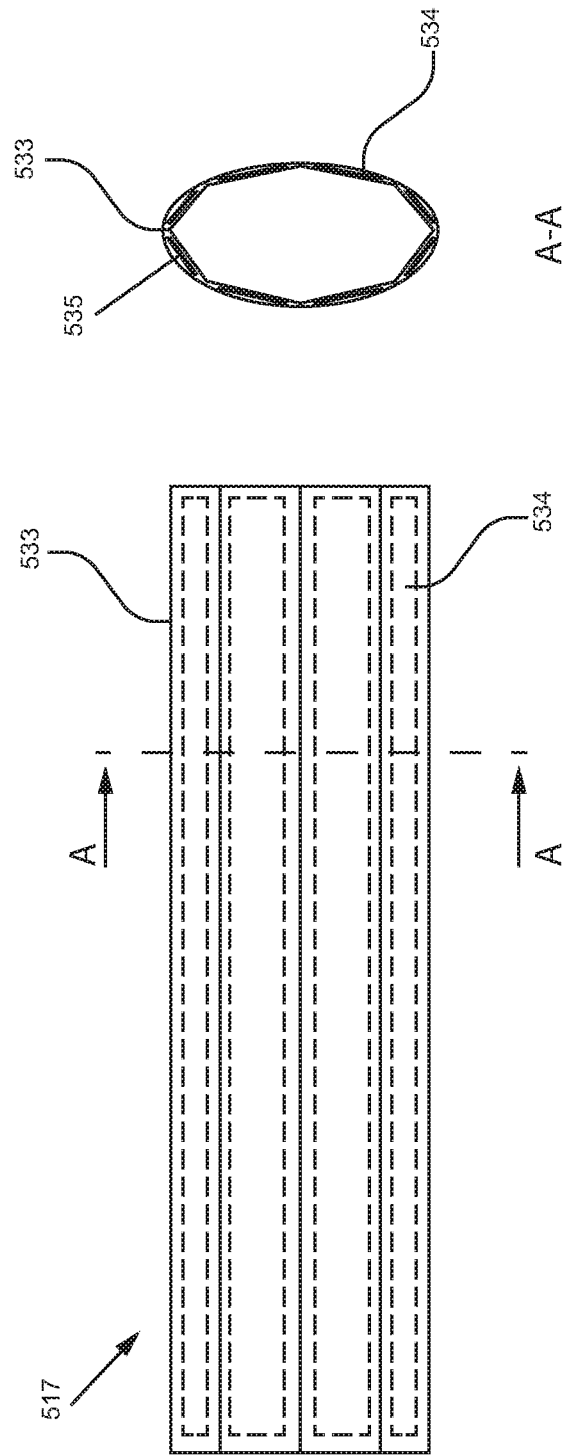

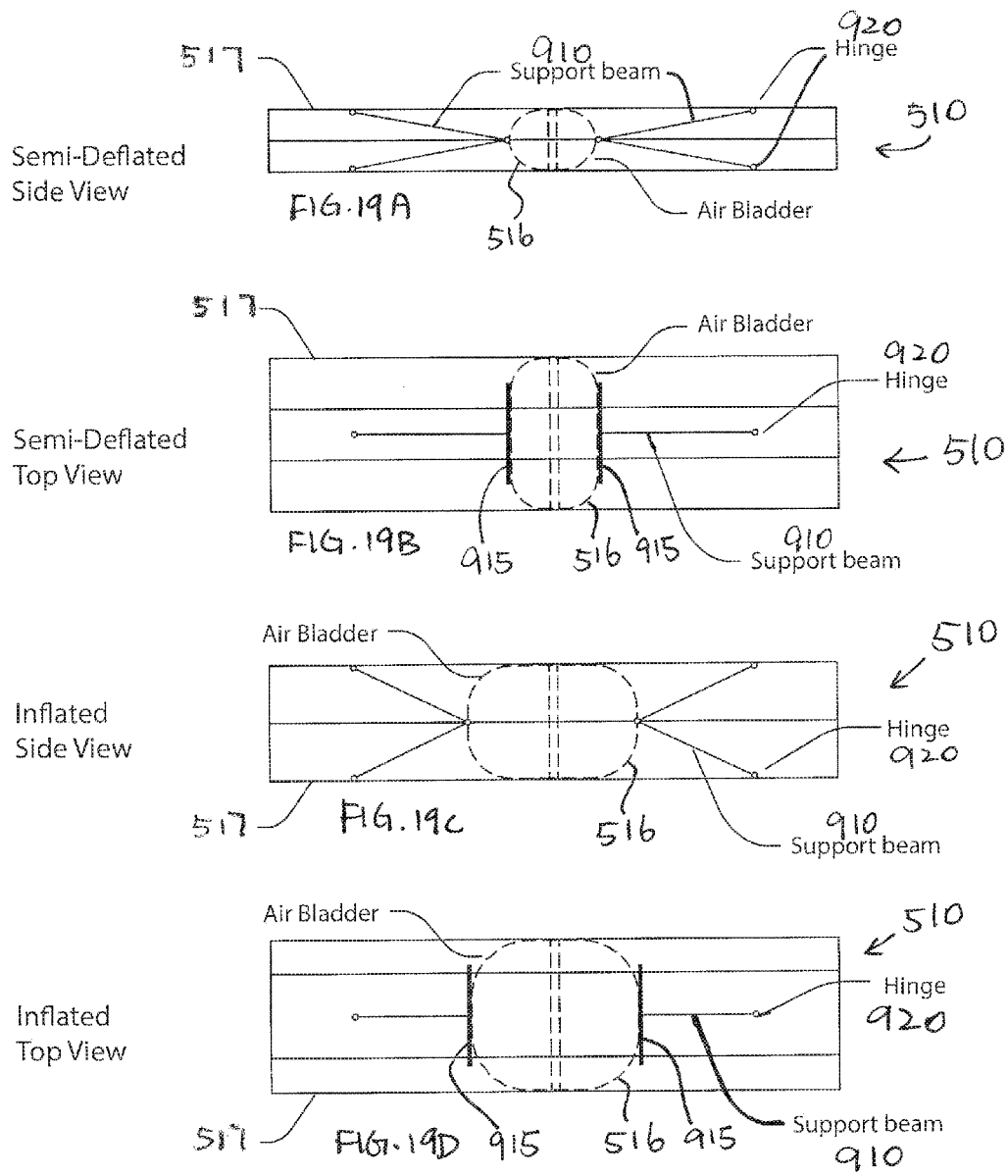

Single Modular piece

Expanded view of Bladder Assembly comprised of connected Modular pieces 3D view of Bladder Assembly
comprised of connected
Modular pieces Deflated Side View Side View Inflated Flattened Top View

APPARATUSES AND METHODS FOR DISRUPTING AND PREVENTING SNORE

CROSS-REFERENCE TO RELATED APPLICATIONS

This application claims the benefit of U.S. provisional patent application No. 62/133,958 filed Mar. 16, 2015, PCT patent application no. PCT/CA2015/050630 filed Jul. 7, 2015, and U.S. provisional application No. 62/294,670 filed Feb. 12, 2016, all of which are herein incorporated by reference in entirety.

FIELD

The present disclosure relates generally to apparatuses and methods for moving the snorer's head when sleeping for disrupting and preventing snoring.

BACKGROUND

Snoring is the vibration of respiratory structures and the resulting sound. The irregular airflow is caused by a narrowing, collapsing or blockage of a passageway and is mostly due to relaxing throat muscles and in some cases is extended to Obstructive Sleep Apnea (OSA).

Statistically, at least 30% of adults snore and rising to 60% of men and 40% of women aged 60 to 65 years; this suggests an increased susceptibility to snoring as age increases.

Snoring is known to cause sleep deprivation to snorers and those around them, as well as daytime drowsiness, irritability, lack of focus and decreased libido. It has also been suggested that it can cause significant psychological and social damage to sufferers. Multiple studies reveal a positive correlation between loud snoring and increased risk of heart attack by about 34%, and increased risk of stroke by about 67%.

Some systems may require specific pillow bodies limiting the pillow options of the user, where the user might have medical or personal preference choosing his/her pillow based on a range of features including size, softness, hardness, rigidity, neck support, air flow, material allergies, etc. In some methods and systems, the displacement component is isolated with limited effective area and may not be effective if user's head is not placed directly on top of the displacement component and elsewhere along the length of the pillow. Furthermore, some systems place the mechanical and hydraulic components of the system, such as pumps and motors, within a pillow body, resulting in loud noise or vibration in close proximity of the user's head. This noise or vibration results in disrupting the sleep of the snorer as well as other individuals in proximity of the system. In addition, the battery and electrical components being housed within the pillow body results in exposing the head of the user to a number of potential harmful elements such as radiation, electromagnetic fields, and such, which can result in headaches and other symptoms.

SUMMARY

In one aspect, an apparatus for disrupting or preventing snoring may include: an inflatable bladder assembly configured to inflate and deflate to move a head of a user; a conduit connected to the bladder assembly and configured to extend at a distance from the bladder assembly; an air inflator connected to the conduit for inflating the bladder assembly through the conduit, the air inflator being at the distance from the bladder assembly when in use to minimize noise, radiation or discomfort for the user; a controller in communication with the air inflator to actuate the air inflator to inflate the bladder assembly; and an audio processor in communication with the controller, the audio processor being configured to detect sound waves and transmit control commands to the controller to trigger cyclical actuation of the air inflator upon a trigger event, the trigger event including detection of a snoring sound or another trigger event.

In another aspect, the bladder assembly may contact a pillow to raise the head of the user in contact with the pillow when in use.

In yet another aspect, the bladder assembly may be configured to inflate such that all components of the bladder assembly are displaced during the inflation.

In still another aspect, an entire top surface of the bladder assembly is configured to rise simultaneously along a vertical axis of the bladder assembly during the inflation.

In one aspect, the bladder assembly may include rigid or semi-rigid segments pivotally hinged together and an internal inflatable chamber to move the hinged segments, wherein the internal inflatable chamber is coupled to the conduit for inflation.

In another aspect, the controller may be configured to actuate the air inflator on or off periodically to provide an inflation cycle with an inflating time and a deflating time, the inflation cycle being initiated once the trigger event is detected.

In yet another aspect, the controller may be configured to control the speed at which the air inflator inflates the bladder assembly at a pre-determined rate to provide different inflation patterns.

In still another aspect, the apparatus may further include an audio sensor or microphone coupled to the audio processor to receive the sound waves.

In one aspect, the bladder assembly may include a sleeve assembly and an inflatable bladder configured to be received within the sleeve assembly.

In another aspect, the sleeve assembly may include a plurality of rigid or semi-rigid segments, each segment being pivotally hinged to an adjacent segment at each end of the segment, such that the inflatable bladder, during the inflation, is configured to expand the plurality of rigid or semi-rigid segments outwardly.

In yet another aspect, the plurality of rigid or semi-rigid segments may be configured to form a cylindrical or polygonal shape.

In one aspect, the plurality of rigid or semi-rigid segments may include at least a first segment with a first width and a second segment with a second width, wherein the first width is greater than the second width, and wherein the first segment is positioned at a bottom of the inflatable bladder when the inflatable bladder is inflated.

In another aspect, the first width has a dimension that is equal to or greater than a corresponding width of the inflated inflatable bladder.

In still another aspect, each segment may be pivotally hinged to an adjacent segment at a flexible component.

In one aspect, the flexible component may include extruded flexible material.

In another aspect, the sleeve assembly comprises a plurality of flexible pockets, each pocket configured to receive a corresponding one of the plurality of rigid or semi-rigid segments within, each of the pockets being hinged to adjacent pockets for pivotal movement during the inflation.

In yet another aspect, the bladder assembly may be collapsible or foldable.

In still another aspect, the rigid or semi-rigid segment may include an elongated bar structure adapted to be received within the corresponding flexible pocket.

In one aspect, the apparatus may include a valve configured to deflate the bladder assembly.

In another aspect, the apparatus may include a soundproof housing to suspend the air inflator using suspension components including one of: a ring, a saddle, and a spring.

In yet another aspect, the air inflator may be configured to expand the bladder assembly to a pre-determined maximum size based on a pressure control.

In still another aspect, the audio processor may couple to one or more microphones and is configured to receive sound waves from a plurality of sources as detected by the one or more microphones, and wherein the audio processor is configured to identify a location of a snorer by analyzing the sound waves from the plurality of sources.

In one aspect, the audio processor may be configured to receive sound waves from a plurality of sources and determine a plurality of corresponding locations of the sources.

In another aspect, the bladder assembly may be configured for placement within an opening of the pillow, under the pillow or having an integrated padding to provide the pillow.

In yet another aspect, the air inflator may be coupled to a wired or wireless transceiver for communication with at least one of the conduit and the controller of the apparatus.

In still another aspect, the audio processor may couple to a wired or wireless transceiver for receiving the sound waves and transmitting the control commands.

In one aspect, the controller may activate a cycle when the snoring sound is detected to trigger a cyclical motion of inflation and deflation.

In another aspect, the inflatable bladder may create movement simultaneously along an entire length of the bladder assembly.

In yet another aspect, the apparatus may include a silencing component to reduce transfer of noise and vibration from the air inflator during the inflation.

In one aspect, a method for disrupting or preventing a user from snoring may include: receiving sound wave by an audio sensing component; analyzing, by a controller in communication with the audio sensing component, said sound wave to determine if a snoring sound has occurred; upon determining that the snoring sound has occurred: activating an air inflator outside of the pillow, by the controller, to inflate and expand an inflatable bladder assembly to cause a pillow to move to a raised position, wherein the bladder assembly is connected to the air inflator through a conduit, the conduit extendable from the bladder assembly at a distance so that the user is not disturbed by any sound of the air inflator being activated; and deactivating the air inflator, by the controller, after a pre-determined period of time, to lower the pillow from the raised position.

In another aspect, the method may include determining, by an audio processor of the controller: that the snoring sound has occurred; and a digital snore signature of the snoring sound by processing the sound waves, the digital snore signature being linked to the user.

In yet another aspect, the digital snore signature may include electronic identification data corresponding to a recognized user.

In still another aspect, the method may include recognizing a user associated with the sound wave and the snoring sound using stored historical sound waves.

In one aspect, the method may include recognizing and filtering the sound wave to discern the snoring sound from other types of sounds.

In another aspect, the method may include receiving confirmation of the detected snoring sound or an error to refine the audio processor using machine learning.

In still another aspect, the method may include correlating the sound waves to additional sound waves received from other devices and stored on a shared or cloud storage device.

In yet another aspect, the method may include actuating the inflatable bladder assembly for different lengths of time and different intervals of time based on one or more inflation patterns.

In one aspect, the method may include: 1) predicting the occurrence of the snoring sound prior to a detection of the snoring sound from the sound waves; and 2) triggering the controller to actuate the inflatable bladder assembly, the prediction based on a snoring profile of a user, the snoring profile comprising at least historical user data.

In one aspect, an apparatus for disrupting or preventing snoring may include: an inflatable bladder assembly configured to inflate and deflate to move a head of user, the bladder assembly having a top surface, such that the entire top surface of the bladder assembly is operable to rise simultaneously during inflation; a conduit connected to the bladder assembly; an air inflator connected to the conduit for inflating the bladder assembly through the conduit when in use; a controller in communication with the air inflator to actuate the air inflator to inflate the bladder assembly; and an audio processor in communication with the controller, the audio processor being configured to detect sound waves and transmit control commands to the controller to trigger actuation of the air inflator upon a trigger event, the trigger event including detection of a snoring sound or another trigger event.

In one aspect, the bladder assembly may contact a pillow to raise the head of the user in contact with the pillow when in use.

In another aspect, the entire top surface of the bladder assembly may be configured to rise at the same rate along a vertical axis of the bladder assembly during the inflation.

In yet another aspect, the bladder assembly may include rigid or semi-rigid segments pivotally hinged together and an internal inflatable chamber to move the hinged segments, wherein the internal inflatable chamber is coupled to the conduit for inflation.

In still another aspect, the bladder assembly may include a sleeve assembly and an inflatable bladder connected to the conduit and configured to be received within the sleeve assembly.

In one aspect, the sleeve assembly may include a plurality of rigid or semi-rigid segments, each segment being pivotally hinged to an adjacent segment at each end of the segment, such that the inflatable bladder, during the inflation, is configured to expand the plurality of rigid or semi-rigid segments outwardly.

In another aspect, the plurality of rigid or semi-rigid segments may be configured to form a cylindrical or polygonal shape.

In one aspect, the plurality of rigid or semi-rigid segments may include at least a first segment with a first width and a second segment with a second width, wherein the first width is greater than the second width, and wherein the first segment is positioned at a bottom of the inflatable bladder when the inflatable bladder is inflated.

In another aspect, the first width has a dimension that is equal to or greater than a corresponding width of the inflated inflatable bladder.

In yet another aspect, each segment may be pivotally hinged to an adjacent segment at a flexible component.

In still another aspect, the flexible component may include extruded flexible material.

In one aspect, the sleeve assembly may include a plurality of flexible pockets, each pocket configured to receive a corresponding one of the plurality of rigid or semi-rigid segments within, each of the pockets being hinged to adjacent pockets for pivotal movement during the inflation.

In one aspect, the bladder assembly or sleeve assembly may be foldable or collapsible.

In another aspect, the bladder assembly may be foldable to reduce a footprint occupied by the bladder assembly.

In another aspect, one or more of the plurality of rigid or semi-rigid segments may include two or more sections, such that the bladder assembly is operable to be folded at least once into a smaller size.

In yet another aspect, the rigid or semi-rigid segment may include an elongated bar structure adapted to be received within the corresponding flexible pocket.

In still another aspect, the air inflator may be configured to expand the bladder assembly to a pre-determined maximum size based on a pressure control.

In one aspect, an apparatus for disrupting or preventing snoring may include: an inflatable bladder assembly configured to inflate and deflate to move a head of user; an conduit connected to the bladder assembly; an air inflator connected to the conduit for inflating the bladder assembly through the conduit when in use; a controller in communication with the air inflator to actuate the air inflator to inflate the bladder assembly; and an audio processor in communication with the controller, the audio processor being configured to process sound waves to recognize a snoring sound from a user and transmit control commands to the controller to trigger actuation of the air inflator.

In one aspect, the controller may be configured to actuate the air inflator on or off periodically upon recognition of the snoring sound to provide an inflation cycle with an inflating time and a deflating time.

In another aspect, the inflation cycle, once initiated, may be configured to complete one cycle of a inflating time and a deflating time regardless of whether additional snoring sound has been recognized.

In another aspect, the audio processor may be configured to filter the sound waves to discern a snoring sound of the user from one or more snoring sounds of one or more people other than the user.

In yet another aspect, the apparatus may include a valve configured to deflate the bladder assembly.

In still another aspect, the audio processor couples to one or more microphones and is configured to receive sound waves from a plurality of sources as received by the one or more microphones, and wherein the audio processor is configured to identify a location of a user by analyzing the sound waves from the plurality of sources.

In one aspect, the audio processor may be configured to receive sound waves from a plurality of sources and determine a plurality of corresponding locations of the sources.

In another aspect, the audio processor may couple to a wireless transceiver for receiving the sound waves and transmitting the control commands.

In another aspect, the controller may activate a cycle when the snoring sound is recognized to trigger a cyclical motion of inflation and deflation.

In yet another aspect, the audio processor may be configured to determine: 1) that the snoring sound has occurred; and 2) an digital snore signature of the snoring sound by processing the sound waves.

In still another aspect, the digital snore signature may include electronic identification data corresponding to a recognized user.

In one aspect, the audio processor may be configured determine that a snoring sound is likely to occur in a pre-determined period of time.

In another aspect, determination that the snoring sound is likely to occur in a pre-determined period of time is based on at least historical user data.

In one aspect, the audio processor may be configured to recognize a user associated with the sound wave and the snoring sound using stored historical sound waves.

In another aspect, the audio processor may be configured to filter the sound wave to discern the snoring sound from other types of sounds, such as non-snoring sounds.

In yet another aspect, the apparatus may include a user feedback receiver to receive confirmation of the recognized snoring sound or an error to refine the audio processor using machine learning.

In still another aspect, the audio processor may be further configured to correlate the sound waves to additional sound waves received from other devices and stored on a shared or cloud storage device.

In one aspect, the audio processor may be configured to: 1) predict the occurrence of the snoring sound prior to a recognition of the snoring sound from the sound waves; and 2) trigger the controller to actuate the inflatable bladder assembly, the prediction based on a snoring profile of a user, the snoring profile comprising at least historical user data.

In one aspect, an apparatus for disrupting or preventing snoring may include: an inflatable bladder assembly configured to inflate and deflate to move a head of a user; an conduit connected to the bladder assembly; an air inflator connected to the conduit for inflating the bladder assembly through the conduit; a soundproof housing to house and suspend the air inflator within, such that the user is free from disturbance from the air inflator when the air inflator is on; a controller in communication with the air inflator to actuate the air inflator to inflate the bladder assembly; and an audio processor in communication with the controller, the audio processor being configured to detect sound waves and transmit control commands to the controller to trigger actuation of the air inflator upon a trigger event, the trigger event including detection of a snoring sound or another trigger event.

In another aspect, the soundproof housing may be configured to suspend the air inflator using suspension components including one of: a ring, a saddle, and a spring.

In another aspect, the ring may comprise foam.

In yet another aspect, the apparatus may include a silencing component to reduce transfer of noise and vibration from the air inflator during the inflation.

BRIEF DESCRIPTION OF THE DRAWINGS

In the drawings, embodiments of the present disclosure are illustrated by way of example. It is to be expressly understood that the description and drawings are only for the purpose of illustration and as an aid to understanding, and are not intended as a definition of the limits of the present disclosure.

Embodiments will now be described, by way of example only, with reference to the attached figures, wherein:

FIGS. 6A and 6B show a schematic view illustrating an example embodiment of a sleeve assembly in an inflated position.

FIGS. 7A and 7B show a schematic view illustrating an example embodiment of a sleeve assembly in a deflated position.

FIG. 19A illustrates a schematic side view of an example semi-deflated bladder assembly with support beams.

FIG. 19B illustrates a schematic top view of an example semi-deflated bladder assembly with support beams.

FIG. 19C illustrates a schematic side view of an example inflated bladder assembly with support beams.

FIG. 19D illustrates a schematic side view of an example inflated bladder assembly with support beams.

DETAILED DESCRIPTION

Embodiments of methods, systems, and apparatus are described through reference to the drawings.

Embodiments described herein relate to a system and method for disrupting or preventing snore by changing a position of user or snorer's head in a cyclical motion in order to interrupt or reduce noise of snoring sounds, thereby improving quality of sleep for both the user and the user's partner who may be sleeping in the same room. In some cases, embodiments described herein may be configured to predict that a user is about to snore, and based on the prediction, to act to pre-emptively reduce noise of snoring sounds. In some cases, embodiments described herein may be capable of preventing a user from snoring.

In some aspect, embodiments described herein may be operable to treat obstructive sleep related breathing disorders such as sleep apnea.

In some aspect, an apparatus is disclosed to determine occurrence of a trigger event prior to inflating a bladder assembly in close proximity to a user's head. The inflating motion of the bladder assembly may be operable to stimulate the throat muscles and open up the user's airway in his or her throat to interrupt and reduce snoring, as a partially blocked (or collapsed) airway may cause snoring. The trigger event can be a detection of a snoring sound, or the determination or prediction that a user is about to snore. As such, an apparatus may be configured to interrupt a user's snoring, reduce noise of a snoring sound from a user, or both.

In one aspect, one or more embodiments described herein may include a bladder assembly that can be used with different pillows, has high portability, and is operable to facilitate a controlled vertical movement of the bladder assembly to reduce sound of snoring of a user. For example, an entire top surface of the bladder assembly may be configured to rise at the same rate along a vertical axis of the bladder assembly to move a user's head during the user's sleep. Moving a user's head may include raising or lowering a user's head, as well as displacing a user's head in any direction relative to a centre point of bladder assembly or pillow.

Figure 1:
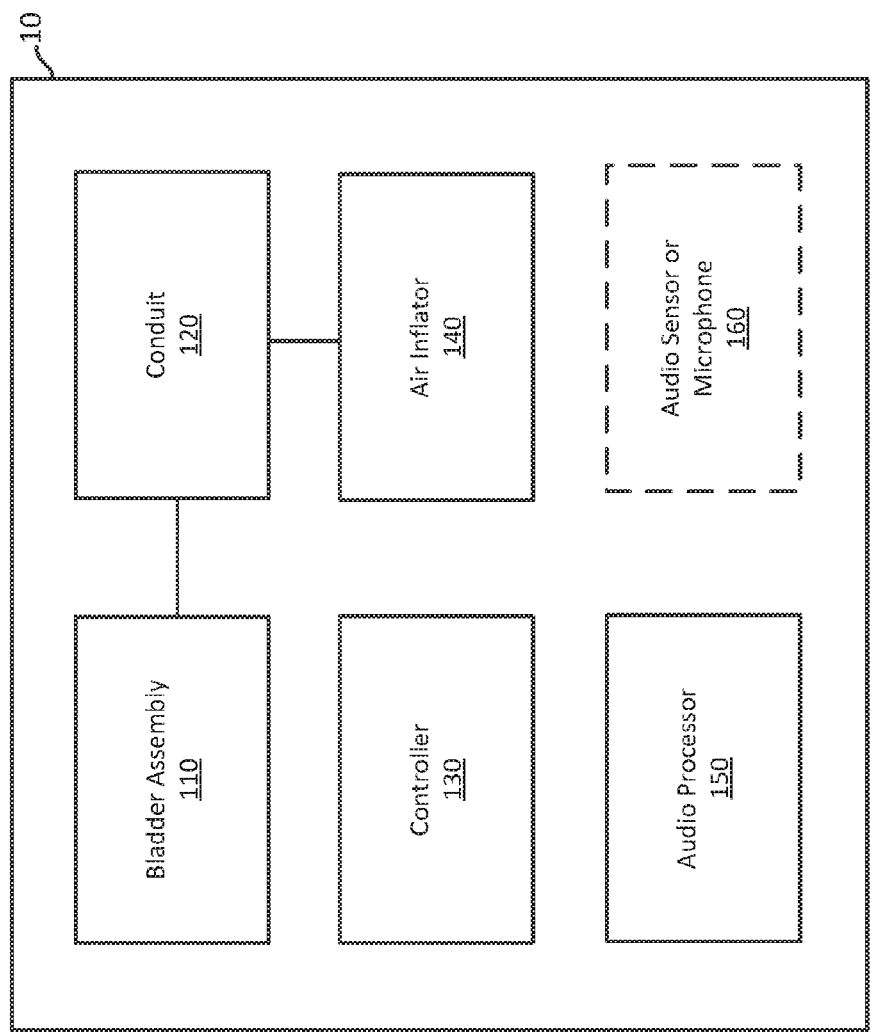
FIG. 1 is an example block schematic diagram of an apparatus for snore disruption or prevention, according to some embodiments.

FIG. 1 is an example block schematic diagram of an apparatus for snore disruption, according to some embodiments.

As shown, an example embodiment of a snore disrupting apparatus 10 may include an inflatable bladder assembly 110, a conduit 120, a controller 130, an air inflator or pump 140, an audio processor 150, and an optional audio sensor or microphone 160. Apparatus 10 may also include a power source.

Inflatable bladder assembly 110 may be configured to inflate and deflate to move a head of a user. For example, bladder assembly 110 may be inflated to raise a head of a user. Conduit 120 may be connected to the bladder assembly and configured to extend at a distance from the bladder assembly. Conduit may be a tube or any suitable means to facilitate liquid or air communication between bladder assembly 110 and air inflator 140. Inflatable bladder assembly 110 may be positioned under or within a pillow of a user in order to move the user's head when in use. Inflatable bladder assembly 110 may also have integrated cushions to provide the pillow for the user. These are examples and other embodiments may have different configurations to contact user to move the user's head when in use.

Air inflator 140 may be connected to conduit for inflating bladder assembly 110 through the conduit 120, air inflator 140 being at the distance from the bladder assembly 110 when in use to minimize noise, exposure to electromagnetic field and radiation or discomfort for a user. The conduit 120 may be a tube, for example, that connects the air inflator 140 and the bladder assembly 110 such that the air inflator may be positioned away from the bladder assembly 110 but may still be connected thereto to trigger inflation thereof. The distance may be in the range of 0.5 to 4 meters, as an illustrative example. The conduit 120 may enable the air inflator 140 to be positioned under a bed or in a drawer, for example.

Figure 13:
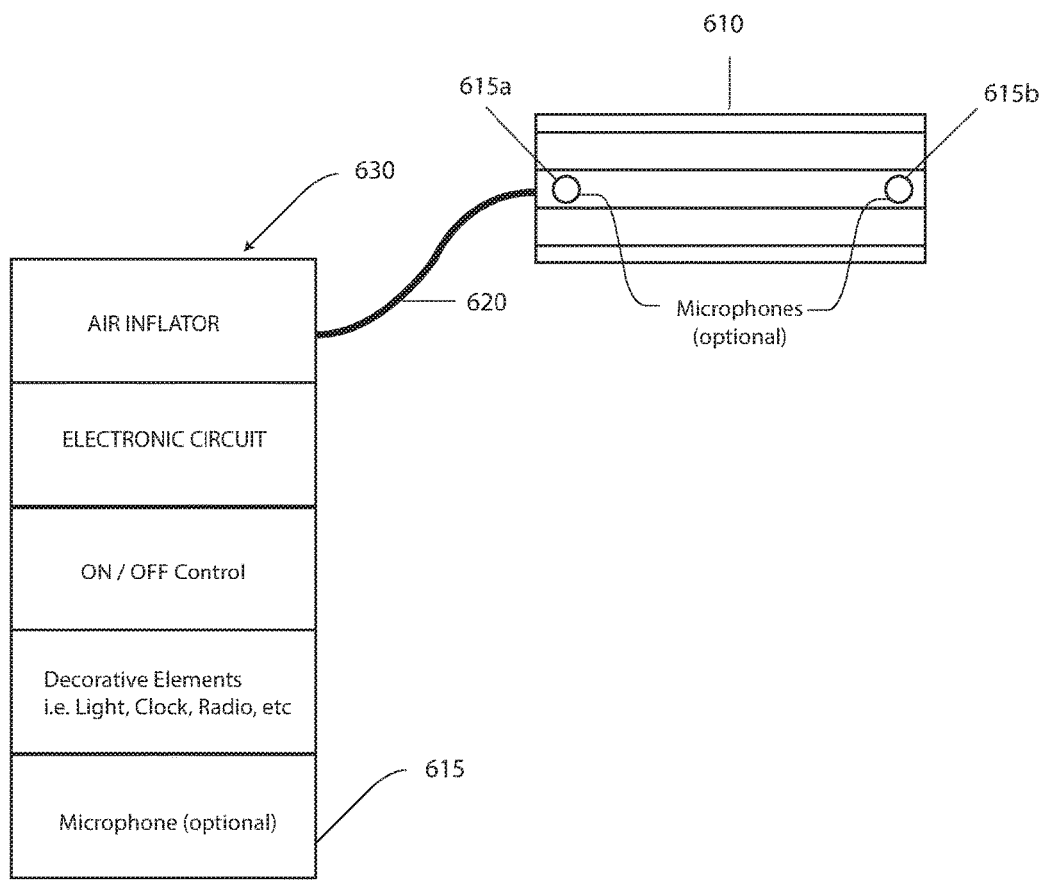
FIG. 13 is another example schematic diagram of an apparatus for snore disruption or prevention with two microphones.

In some embodiments, for example as shown in FIG. 13, all electronic or noisy components such as air inflator 140, electronic circuits, on/off control, on/off control, and optional decorative components such as light, clock, radio and so on may be housed in a housing 630 and placed relatively close to the user, if a pre-determined minimal level of noise, radiation, and electromagnetic field reaches the user from housing 630 while the apparatus is on.

Referring back to FIG. 1, in some embodiments, air inflator 140 may be a low-noise air pump, as to minimally disturb a user who is sleeping.

Controller 130 may be in communication with air inflator 140 to initiate or actuate air inflator 140, which when actuated, may inflate inflatable components of the bladder assembly 110 to cause movement of user's head to interrupt or reduce a noise caused by snoring.

Audio processor 150 may be in communication with controller 130. The audio processor 150 is configured to detect sound waves emanating from user and process the sound waves to detect a trigger event. The audio processor 150 may process the sound waves by filtering out other sounds not relating to the user or snoring. The audio processor 150 may transmit control commands to controller 130 to trigger cyclical actuation of air inflator 140 upon detection of the trigger event. An example trigger event may be detection of a snoring sound or another trigger event, such as a prediction of a snoring sound for a user, a predefined cycle or time based trigger event (e.g. every hour, at certain times).

For example, a cyclical actuation of air inflator 140 may cause air inflator 140 to start a cyclical motion, e.g. one or more cycles of inflation and deflation. For example, a cyclical motion may include one or more rounds of inflation and deflation. One round of inflation and deflation may include 1) one or more periods during which air inflator 140 is pumping air into bladder assembly 110 via conduit 120 ("inflation"); and 2) one or more periods during which air inflator 140 is deactivated, causing bladder assembly 110 to deflate or at least maintain a current level of volume ("deflation"). In some embodiments, one round of inflation and deflation may have a pre-determined pattern of inflation and deflation. A pattern of inflation and deflation may be, for example, 20 seconds of inflation followed by 10 seconds of deflation. Another pattern of inflation and deflation may be, for example, 10 seconds of inflation, 10 seconds of deflation, and 15 seconds of inflation. Within a cyclical motion, each round of inflation and deflation may have a different pattern. In some embodiments, a cyclical motion may only have inflation patterns or deflation patterns, or both inflation and deflation patterns. Inflation and deflation patterns in a cyclical motion may be pre-determined, or user-customized, or crowd-sourced based on historical user data from one or more users.

In some embodiments, audio processor 150 may include an internal audio sensor or microphone for detecting sound waves, or may connect to an external audio sensor for receiving sound waves. For example, the external audio sensor may be a microphone in a smart phone or "Internet of Things" device that may be positioned proximate to the user to receive sound waves emanating from the user.

In some embodiments, apparatus 10 may further include an integrated audio sensor or microphone 160 coupled to audio processor 150 for receiving sound waves and transmitting said sound waves to audio processor 150.

In some embodiments, one or more of controller 130, audio processor 150 and audio sensor 160 may be part of a consumer electronic device such as a laptop, a mobile phone, a smart device, or bespoke device that may be configured to communicate to the rest of the apparatus 10 in a wired or wireless setting.

In some embodiments, audio processor 150 may be coupled to a wireless transceiver for receiving the sound waves and transmitting the control commands. This may enable audio processor 150 to be positioned proximate to the user to receive sounds waves while the other components (particularly components that may make noise or emit radiation) may be positioned further from the user while still being coupled to the audio processor 150.

In some embodiments, air inflator 140 may be coupled to a wireless transceiver for communication with at least one of conduit 120 and controller 130 of the apparatus 10.

In some embodiments, air inflator 140 may be integrally connected to audio processor 150. For example, an air inflator 140 may have a design that may be optimized to reduce noise or radiation so may be proximate to the user without causing disruption.

In some embodiments, bladder assembly 110 may be configured to contact a pillow to move or raise the head of the user that is in contact with the pillow when in use. The pillow may or may not include a pillow case. In some embodiments, bladder assembly 110 may be configured for placement within an opening of the pillow, under the pillow or having an integrated padding providing the pillow. In some embodiments, bladder assembly 110 may serve as a pillow for a user. For example, bladder assembly 110 may include padding or cushioning material to serve as a pillow.

In some embodiments, air inflator 140 is placed at a distance from the user, the distance being sufficiently far from the user that when activated or in operation, any sounds or vibrations from air inflator 140 would not disturb the user or anyone in close proximity to the user. For example, air inflator 140 may be placed approximately 1 to 3 meters from the user's head. This is an illustrative example distance. For example, air inflator 140 may be placed on the floor, and connected via conduit 120 to bladder assembly 110, which is in close proximity to the user's head.

In some embodiments, controller 130, audio processor 150 or audio sensor 160 may also be placed at a distance from the user in order to avoid potential harmful effects such as radiation or magnetic fields. For example, one or more of controller 130, audio processor 150 and audio sensor 160 may be placed within the same housing as air inflator 140, or in a separate housing away from the user.

In some embodiments, air inflator 140 may be placed within a housing that can prevent (reduce) noise and vibration from reaching a user in proximity therewith. Air inflator 140 may include a pump which may cause noise with inflating bladder assembly 110. For example, a soundproof housing may be used to house and suspend air inflator 140 within, such that the user is free from disturbance from the air inflator when the air inflator is on. Air inflator 140 may be suspended in mid-air, such that gas in the air may muffle or otherwise reduce the volume of sound.

In one embodiment, the soundproof housing may be configured to suspend the air inflator using suspension components including one of a ring, a saddle, and a spring that may contact the air inflator 140 to suspend within the housing.

Referring now to FIGS. 9A to 9E, which show various embodiments of a suspended air inflator 140 within a housing. As can be seen, air inflator 140 may be suspended from a surface 190 by suspension components 910, 920. Surface 190 may be a ground surface or a bottom surface of a soundproof housing (e.g. housing 630 in FIGS. 10-15). Air inflator 140 may be suspended at two ends 180a, 180b.

Figure 9A:
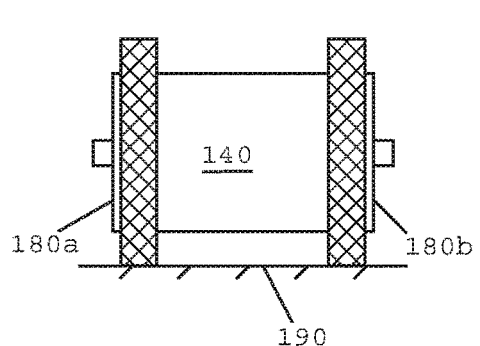
FIGS. 9A and 9E illustrate an example embodiment of an air inflator suspended by foam.
Figure 9E:
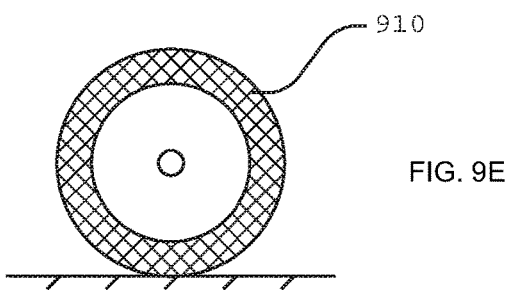

In FIGS. 9A and 9E, each end 180a, 180b of air inflator 140 is supported by a suspension component 910 made of foam or similar material. Foam may absorb vibration or other types of movement, as to reduce or eliminate noise from movements of air inflator 140.

Figure 9B:
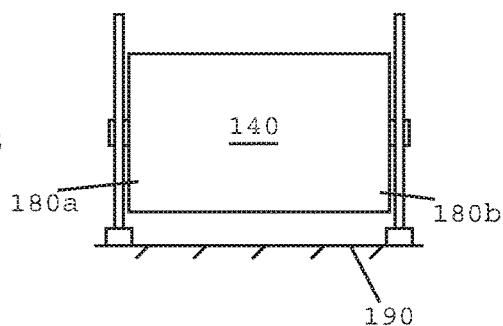
FIGS. 9B and 9F illustrate an example embodiment of an air inflator suspended by spring.
Figure 9F:
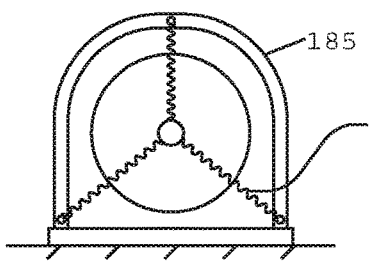

In FIGS. 9B (and 9F) 9C (and 9G) and 9D (and 9H) each end 180a, 180b of air inflator 140 is supported by a support structure 185 and a suspension component 920. Suspension component 920 may be made of spring or another type of resilient device that may absorb or eliminate movements of air inflator 140. Support structure 185 may be a rigid structure that is capable of holding or supporting the weight of air inflator 140 for a prolonged period of time. In FIGS. 9B and 9F, a first end of each of three suspension components 920 is connected or coupled to the air inflator 140 at a position proximate the center of a first end 180a of air inflator 140, and a second end of each of the three suspension components 920 is connected or coupled to a support structure 185 at different locations on the support structure 185. Similar suspension mechanism is done at the second end 180b of air inflator 140. This way, support structure 185 can safely hold air inflator 140 in mid-air as not to physically contact any part of housing 630, so that vibrations or noise escaping the housing of air inflator 140 may be reduced or eliminated. Movements of air inflator 140 may also be dampened since movements may be absorbed by suspension components 920.

Figure 9C:
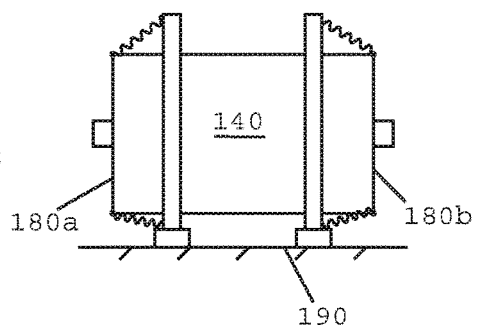
FIGS. 9C and 9G illustrate another example embodiment of an air inflator suspended by spring.
Figure 9G:
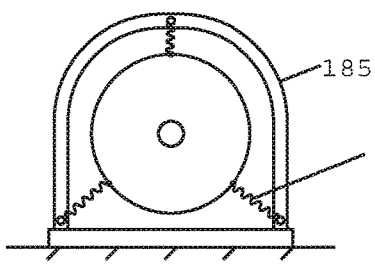
Figure 9D:
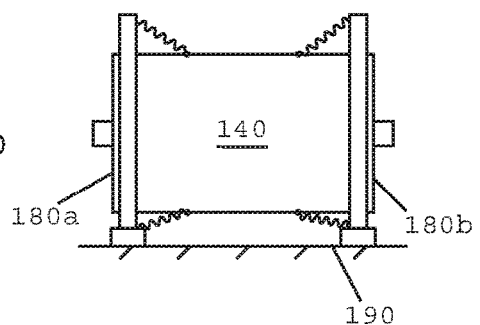
FIGS. 9D and 9H illustrate yet another example embodiment of an air inflator suspended by spring.
Figure 9H:
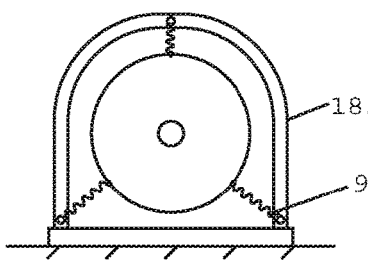

In FIGS. 9C (and 9G) and 9D (and 9H) support structures 185 are shown to be placed at different locations relative to a vertical center of air inflator 140. Each suspension component such as spring 920 may be coupled at one end to support structure 185 and at the other end to any suitable locations on air inflator 140, as long as positioning of the two support structures 185 are more or less symmetrical with respect to the vertical center of air inflator 140 to achieve a balanced load in suspension.

Even though three suspension components 920 are shown in FIGS. 9B (and 9F) 9C (and 9G) and 9D (and 9H) the number of springs that may be used to suspend air inflator 140 may be less or more than three. For example, two suspension components 920 may be used for each end 180a, 180b. For another example, four suspension components 920 may be used for each end 180a, 180b.

In another embodiment, apparatus 10 may further include a silencing component (see for example FIG. 5 silencing component 519) to reduce transfer of noise and vibration from the air inflator to surrounding environment when air inflator is on, so that one or more users are not disturbed during sleep.

Figure 25:
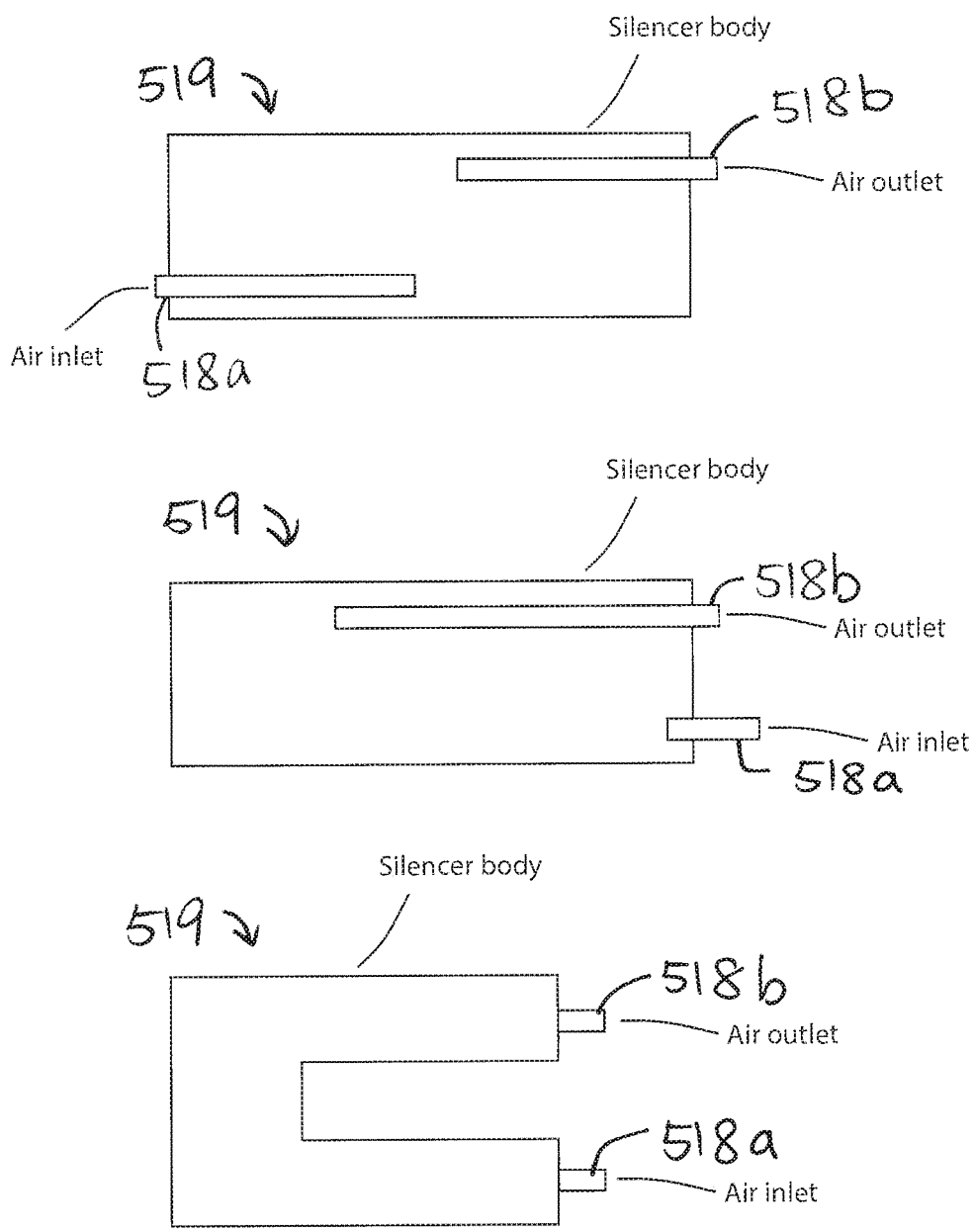
FIG. 25 illustrates various examples of a silencing component.

Referring now to FIG. 25, which illustrate various example embodiments of a silencing component 519. The silencing component may be positioned on conduit 120, 518 to reduce the noise of the vibration of gas that may pass through to inflate the bladder assembly 110, 510. An air inlet 518a and an air outlet 518b may be connected to conduit 120, 518 and housed within silencing component 519 to reduce noise generated by air inflator 140 or conduit 120, 518.

A silencing component may be similar in nature to a car exhaust pipe silencer, or any other suitable silencing structure that includes two or more chambers to silence vibrations.

In some embodiment, air inflator 140 may not be required to be placed at a distance from the user, with either the soundproof housing or the silencing component, since the noise or vibration coming from air inflator 140 may be greatly reduced by either the housing or the silencing component or design of the air inflator 140.

In some embodiments, controller 130 may be configured to actuate the air inflator 140 on or off periodically to provide an inflation cycle. The inflation cycle may have an inflating time and a deflating time, the inflation cycle being initiated once the snoring sound or other trigger event detected. The inflating time may be the time to inflate the bladder assembly 110 and the deflating time may be the time to deflate the bladder assembly 110. The inflating time may be different from the deflating time, or may be the same depending on how long it takes to inflate the bladder assembly 110 and deflate the bladder assembly 110.

In some embodiments, controller 130 may be configured to control the speed at which the air inflator 140 inflates the bladder assembly 110 at a pre-determined rate to provide different inflation patterns. Inflation patterns may include a variety of patterns, each pattern including an inflation and corresponding deflation during a cycle, as well as other types of inflation characteristics such as speed of inflation for each cycle. In some embodiments, an inflation pattern may include information regarding multi-cycles, such as frequency of cycles. An inflation pattern may be linked to different trigger events such that different inflation patterns may be used depending on the detected trigger event. For example, for some users a better result may be achieved with a slow-rise inflation pattern, while for another user a high-rise pillow after inflation may be optimal. In some cases, the inflation patterns may not be dictated by user preference alone. For example, the reason for using different patterns or speeds may be to achieve optimized performance of the apparatus. The settings may be controlled or adjusted by the user or automatically by controller 130. Inflation patterns may be stored locally within controller 130 or remotely, for example, on a database 220 accessible via network 210.

In some embodiments, once an inflation cycle has been initiated or activated by controller 130, air inflator 140 may be configured to proceed to complete the entire cycle at least once, regardless of whether a new trigger event has been detected (e.g. determination of a new snoring sound) prior to completion of the cycle.

In some embodiments, controller 130 may be configured to set a pre-determined number of cycles to complete prior to detection of additional trigger events. For example, once a trigger event is detected the a cycle may commence and any additional trigger events may be ignored (even temporarily) until the cycle finishes without triggering re-start of the cycle mid-way through a cycle that has already commenced. After the cycle completes then it may restart if a trigger event was detected mid-way in the cycle. This may be based on a default setting or user preference, for example.

In some embodiments, apparatus 10 may further include a valve configured to deflate the bladder assembly 110. This may trigger the start of the deflation cycle for example. The apparatus 10 may further include additional components to facilitate deflation of the bladder assembly 110 to, for example, compress the bladder assembly 110 during the deflation cycle.

Figure 5:
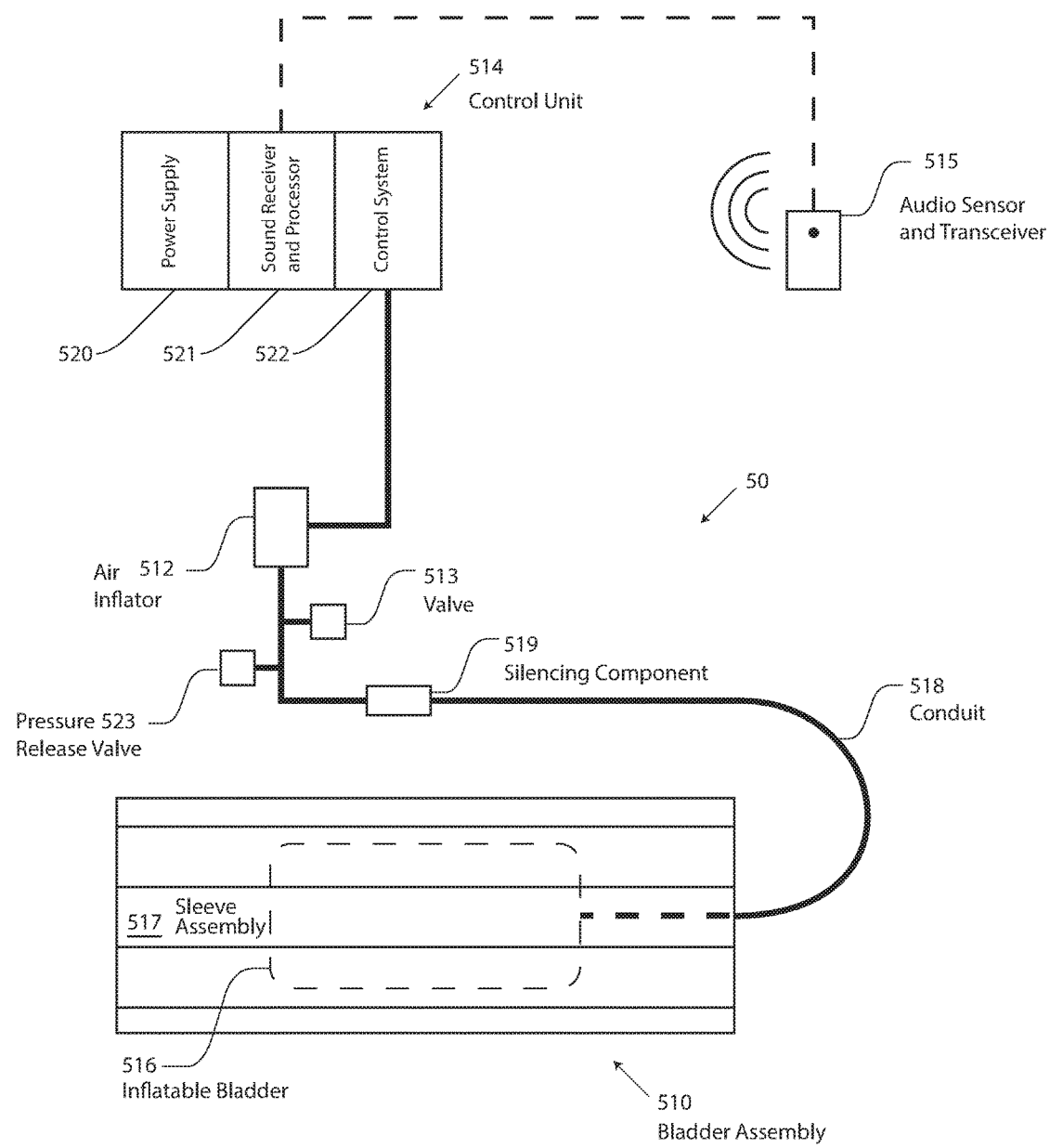
FIG. 5 is an example schematic diagram of another apparatus for snore disruption or prevention, according to some embodiments.
Figure 24:
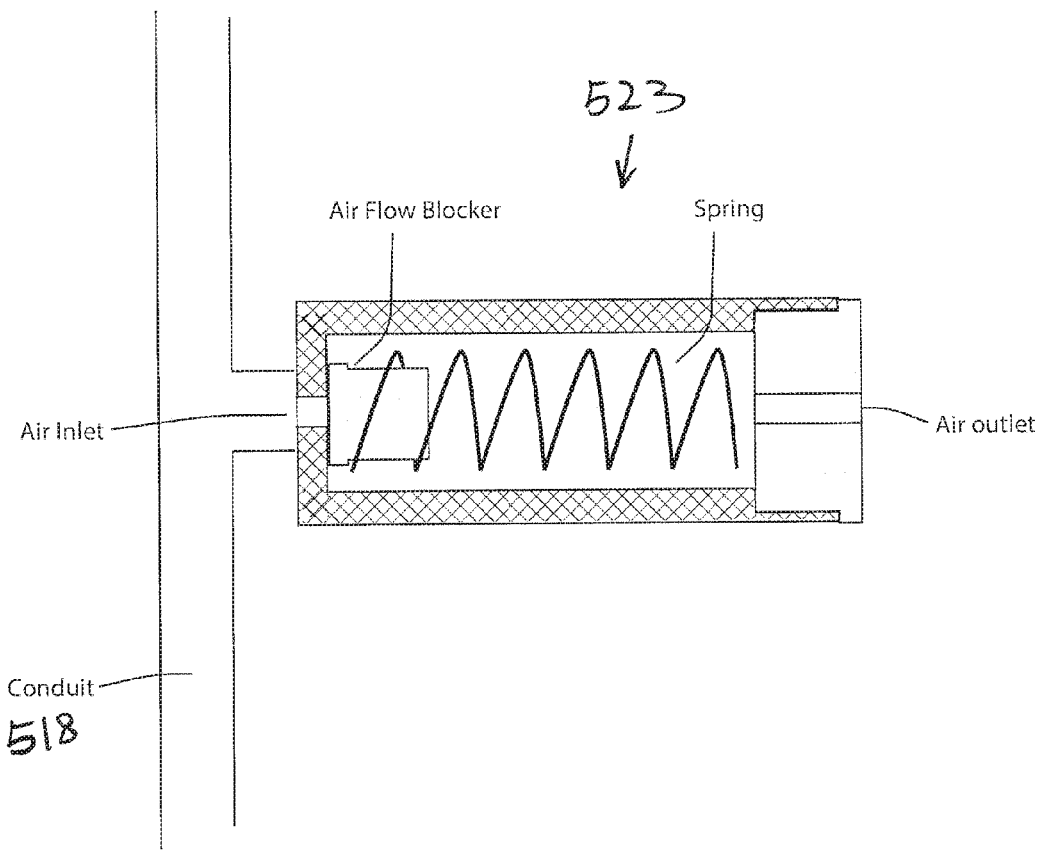
FIG. 24 is a schematic illustration of an example pressure release valve.

In some embodiments, air inflator 140 may be configured to expand bladder assembly 110 to a pre-determined maximum size based on pressure control. The pressure control may be pre-determined by user setting or as a default setting. Pressure control may ensure that bladder assembly 110 or a pillow in use with the bladder assembly 110 is not over expanded or damaged in any manner. For example, the pressure control may be performed by a pressure release valve 523, which is shown in FIG. 5. A pressure release valve may be for example a standard industry component, see for example FIG. 24, which demonstrate an example pressure release valve 523 connected to a conduit 518. Through the use of an air flow blocker and a spring, pressure control may be achieved.

In some embodiments, audio processor 150 may be configured to receive sound waves from a plurality of sources and determine a plurality of corresponding locations of the sources. This may help audio processor 150 identify source of snoring sound if there are multiple people in the same room for example. This may also help audio processor 150 filter out sounds that do not emanate from the user if the user location is known, for example, and different from a detected location of another source of sound waves.

In some embodiments, additional sensors might be in communication with the device to improve detection of snoring or predict snoring based on historical data from the user or other users. Additional sensors may be part of the apparatus or the data can be received from other products that measure and communicate biological or bio-signal data such as heart rate, brain waves and EEG readings, and body heat. Some components may be in "sleep" mode until the apparatus determines the user is sleeping. For example, sensors that sense biological or bio-signal data (pulse, brainwaves) may be used to determine that the user is sleeping (e.g. sleep state) or in a deep sleep state that may increase likelihood of snoring, which may be used to predict snoring.

In some embodiments, audio processor 150 and controller 130 may be configured to be part of the same device or component to integrate processing of sound waves and activation of inflation.

In some embodiments, audio processor 150 may be coupled to one or more audio sensors or microphones 160 and configured to receive sound waves from a plurality of sources as detected by the one or more microphones 160. The audio processor 150 may be configured to identify a location of a snorer by analyzing the sound waves from the plurality of sources.

Apparatus 10 may also include an ON/OFF switch, either as a standalone device, or as part of audio processor 150, audio sensor 160 or controller 130, to turn apparatus 10 on or off.

In some embodiments, one or more components of apparatus 10 may be equipped with additional sensors such as motion sensor, light sensor, heat sensor, humidity sensor, air particle sensor, proximity sensor, and so on.

In some embodiments, one or more components of apparatus 10 may be equipped with a digital display to provide reports, a current time, detected snore sounds, and other information to a user.

In some embodiments, controller 130 may be configured to record and store user snoring patterns. The user snoring patterns may provide a digital snore signature for the user. The digital snore signature may be unique to the user in order to recognize sound waves emanating from the user and filter out sound waves from other sources. The signature may include frequency range, loudness, or patterns of snoring. Controller 130 may be further configured to transmit the stored user information to other devices such as mobile phones, computers, or laptops over wired or wireless communication.

Figure 2:
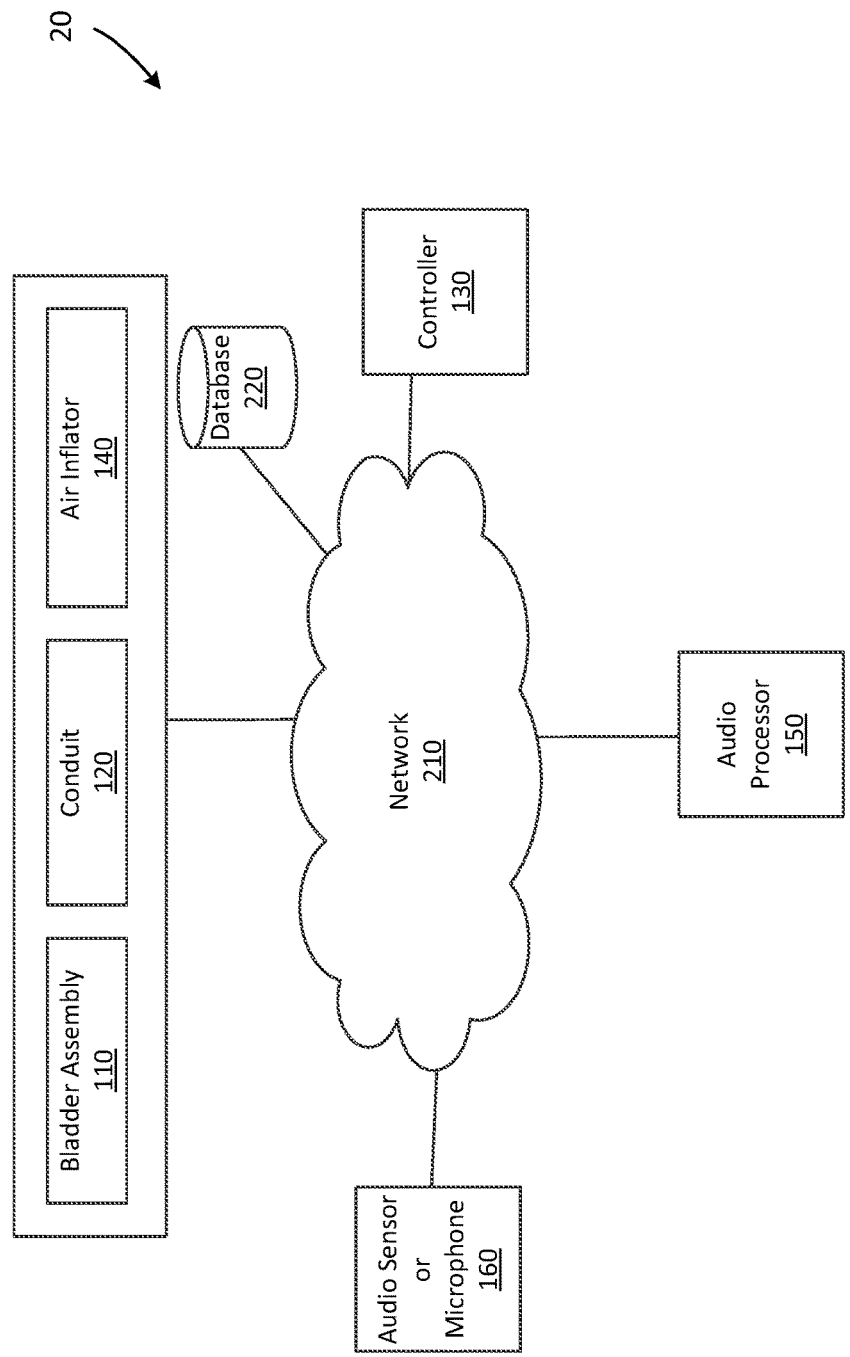
FIG. 2 is another example schematic diagram of an apparatus for snore disruption or prevention, according to some embodiments.

FIG. 2 is another example schematic diagram of an apparatus 20 for snore disruption or prevention, according to some embodiments. Apparatus 20 may include an inflatable bladder assembly 110, a conduit 120, a controller 130, an air inflator or pump 140, an audio processor 150, and an audio sensor or microphone 160 distributed across a network 210. Database 220 may be provided to store user information and other electronic data. Database 220 may reside on a physical data storage device. Database 220 may store data relating to multiple users and correlate data to detect trends and patterns in data across multiple users. Machine learning techniques may be used to refine processing by audio processor 150 to improve detection trigger events to predict snoring.

Various components of apparatus 20, such as controller 130, audio processor 140 and audio sensor 160 may be implemented using hardware and software, individually or in combination, and may be fixed and/or provided in various electronic forms, such as on non-transitory computer-readable media having instructions stored thereon, distributed network resources (e.g., in a "cloud computing" arrangement or a spoke-and-hub topology), and web service. In some embodiments, the system may be provided using a centralized cloud server, having various endpoint devices that it may communicate and/or control. In some embodiments, the system may be provided in the form of an ad-hoc network operating across one or more computing devices.

Figure 3:
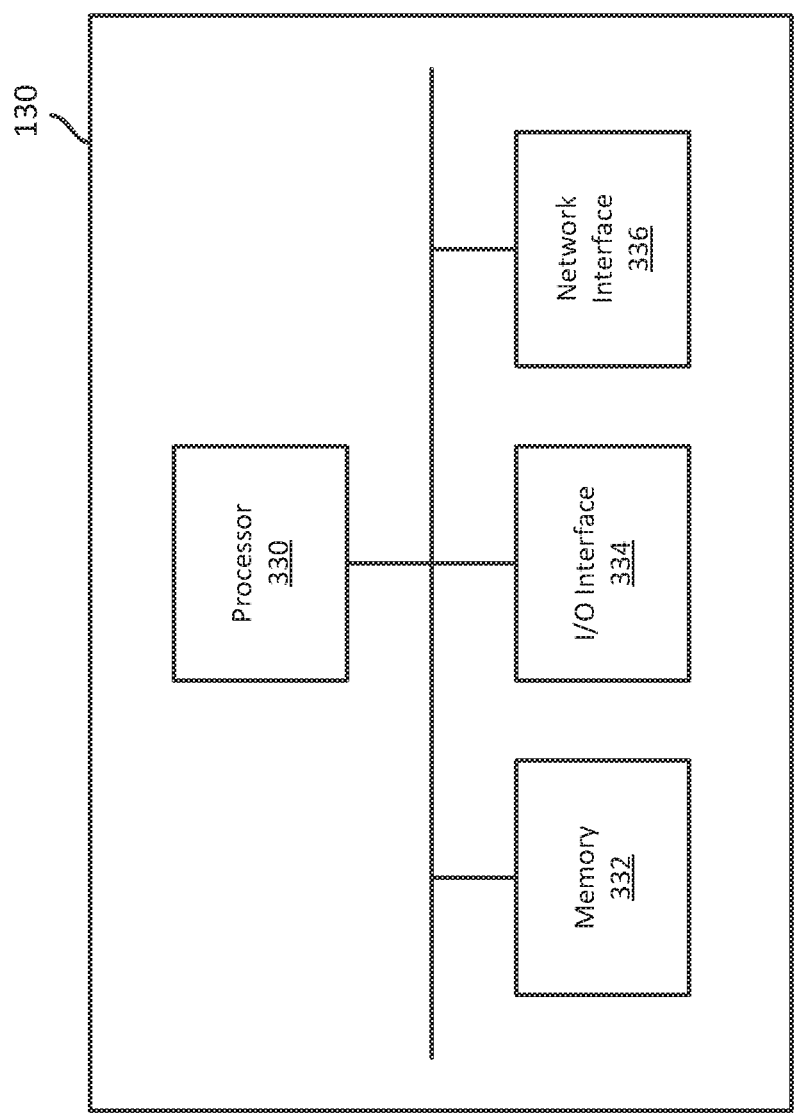
FIG. 3 is an example schematic block diagram of a controller.

FIG. 3 is an example block schematic diagram of a controller. In an embodiment, controller 130 may be implemented using one or more computing devices. The computing devices may be the same or different types of devices. The computing device may include, for example, at least one processor, a data storage device (including volatile memory or non-volatile memory or other data storage elements or a combination thereof), and at least one communication interface. The computing device components may be connected in various ways including directly coupled, indirectly coupled via a network, and distributed over a wide geographic area and connected via a network (which may be referred to as "cloud computing").

For example, and without limitation, the computing device may be a server, network appliance, embedded device, personal computer, or any other computing device capable of being configured to carry out the methods described herein.

FIG. 3 is a schematic diagram of an example computing device that may be used to implement controller 130, exemplary of an embodiment. As depicted, computing device may include at least one processor 330, memory 332, at least one I/O interface 334, and at least one network interface 336. Although this figure relates to a controller 130, in some embodiments audio processor may including similar hardware components to receive and process sound waves to detect trigger events from snoring sounds. For example, I/O interface 334 may connect to one or more microphones to receive sound waves for processing.

Each processor 330 may be, for example, any type of general-purpose microprocessor or microcontroller, a digital signal processing (DSP) processor, an integrated circuit, a field programmable gate array (FPGA), a reconfigurable processor, or any combination thereof. As noted, for audio processor, the processor 330 may be configured to execute code instructions to implement processes for detecting snoring events or other trigger events, as will be described herein.

Memory 332 may include a suitable combination of any type of computer memory that is located either internally or externally such as, for example, random-access memory (RAM), read-only memory (ROM), compact disc read-only memory (CDROM), electro-optical memory, magneto-optical memory, erasable programmable read-only memory (EPROM), and electrically-erasable programmable read-only memory (EEPROM), Ferroelectric RAM (FRAM) or the like.

Each I/O interface 334 enables controller 130 to interconnect with one or more components, input devices, such as a keyboard, mouse, camera, touch screen and a microphone, or with one or more output devices such as a display screen and a speaker.

Each network interface 336 enables controller 130 to communicate with other components (such as audio processor, conduit, for example), to exchange data with other components, to access and connect to network resources, to serve applications, and perform other computing applications by connecting to a network (or multiple networks) capable of carrying data, e.g., one more networks 210.

In some embodiments, controller 130 may be implemented as a physical or virtual instance using various distributed-resource technologies, such as "cloud computing". Potential benefits to cloud computing include ease of adding or removing resources, load balancing, and so on.

Figure 4B:
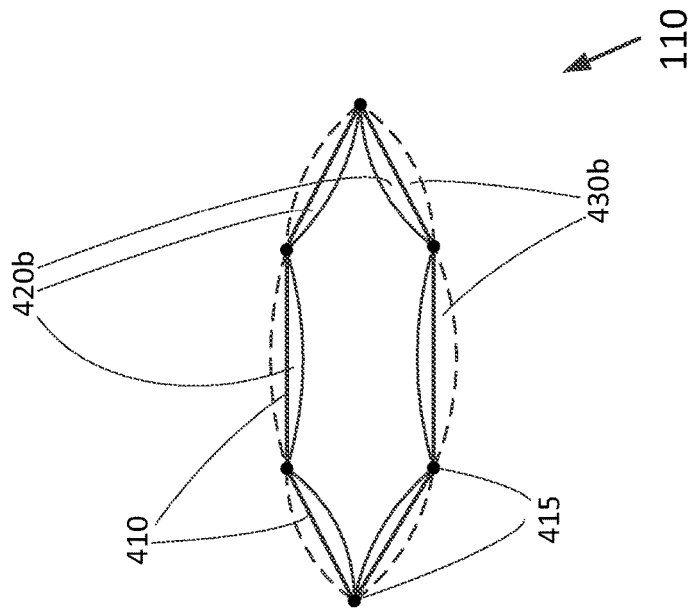
FIG. 4B is a schematic cross-sectional view of an example bladder assembly when deflated.
Figure 4A:
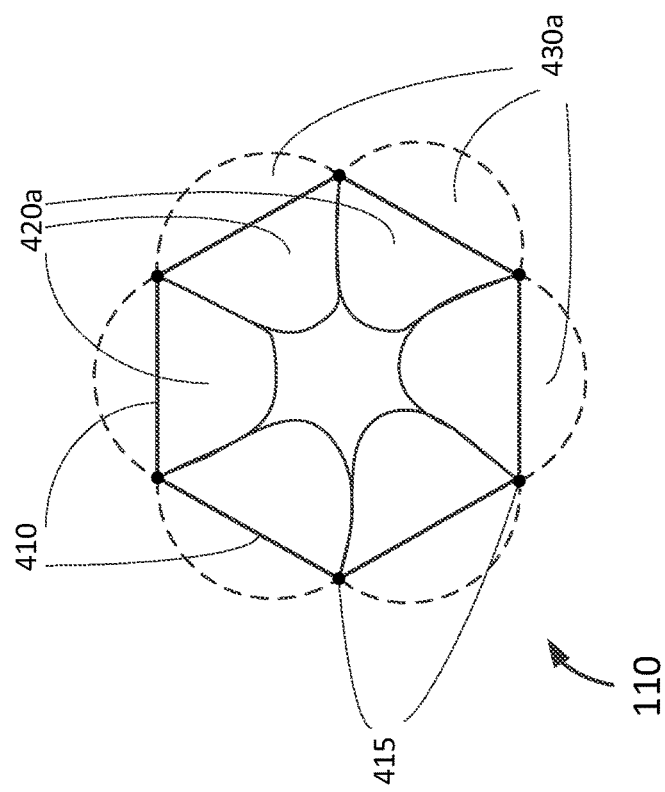
FIG. 4A is a schematic cross-sectional view of an example bladder assembly when inflated.
Figure 4C:
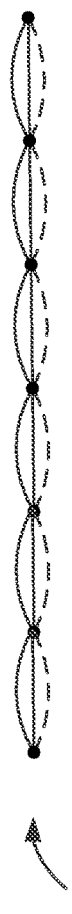
FIG. 4C is a schematic cross-sectional view of an example bladder assembly when flattened.

Referring now to FIG. 4A, which is an example cross-sectional view of a bladder assembly 110 when inflated in accordance with some embodiments. FIG. 4B is an example cross-sectional view of a bladder assembly when deflated. FIG. 4C is an example cross-sectional view of a bladder assembly when flattened.

In some embodiments, bladder assembly 110 may comprises rigid or semi-rigid segments 410 pivotally hinged together and an internal inflatable chamber 420a, 420b to move or displace the hinged segments, where internal inflatable chamber 420a, 420b is coupled to conduit 120 for inflation.

In some embodiments, the plurality of rigid or semi-rigid segments 410 may be configured to form a cylindrical or polygonal shape when inflated.

The rigid or semi-rigid segments 410 may be a structure that is sufficiently strong to sustain weight of a user's head. For example, each segment 410 may be a bar structure made from wood, steel, polyester, carbon fiber, and so on.

In some embodiments, bladder assembly 110 may include optional external chamber 430a, 430b for providing padding or cushion for a user's head. The external chamber 430a, 430b may be inflatable or may include non-inflatable paddings.

The optional external chamber 430a, 430b may provide additional comfort for a user as his or her head is rested against bladder assembly 110. As shown in FIG. 4A, as the external chambers 430a are inflated, they provide some padding or cushion.

In some embodiments, each segment 410 may be pivotally coupled to or an adjacent segment 410 at a flexible component 415. The flexible component 415 may also be referred to as a hinge 415 in this disclosure. The internal chambers 420a, 420b and pivotal connections at the flexible components 415 may enable a smooth, consistent inflating motion of bladder assembly 110, such that when air inflator 140 is pumping air into bladder assembly 110 via conduit 120, all components of bladder assembly 110 are configured to rise at around the same rate, ensuring a level and steady rising motion across substantial amount or entire top surface of bladder assembly 110. This way, disruption to the user is minimal when bladder assembly 110 causes his head to rise up.

In some embodiments, the flexible components 415 may be a relatively thin and soft component compared to rigid or semi-rigid segments 410. Segments 410 and flexible components 415 may be integrally formed or extruded.

In some embodiments, the flexible components 415 may be made from extruded flexible material.

In some embodiments, bladder assembly 110 may contain no rigid or semi segments.

For example, bladder assembly 110 may contain one or more relatively inflatable bladders without any rigid components. In effect, a combination of multiple bladders that expand during inflation, at all or substantially all parts, simultaneously due to a structural design of the soft fabric or bladder assembly itself may create a tension that may be sufficient to support and raise a user's head a higher position.

Prior to inflation by air inflator 140 through conduit 120, bladder assembly 110 may be collapsed or folded, see e.g. FIG. 4B. When air is pumped into internal inflatable chamber 420b, internal inflatable chamber 420b becomes expanded or inflated to arrive at expanded internal inflatable chamber 420a as shown in FIG. 4A. Segments 410 are consequently raised to a higher position relative to a level ground and thus capable of raising a user's head which may be placed on top of bladder assembly 110.

Bladder assembly 110 may be foldable or collapsible. For example. FIG. 4C shows a bladder assembly 110 that is flattened and easy to carry in one embodiment. Other configurations of bladder assembly 110 may be suitable for a foldable or collapsible mechanism.

In some embodiments, bladder assembly 110 may be foldable longitudinally in one or more place so that the assembly can be folded into a smaller size and packed for convenience. This foldable configuration may be achieved by using rigid blades or segments to section bladder assembly 110 into multiple smaller sections.

Figure 18:
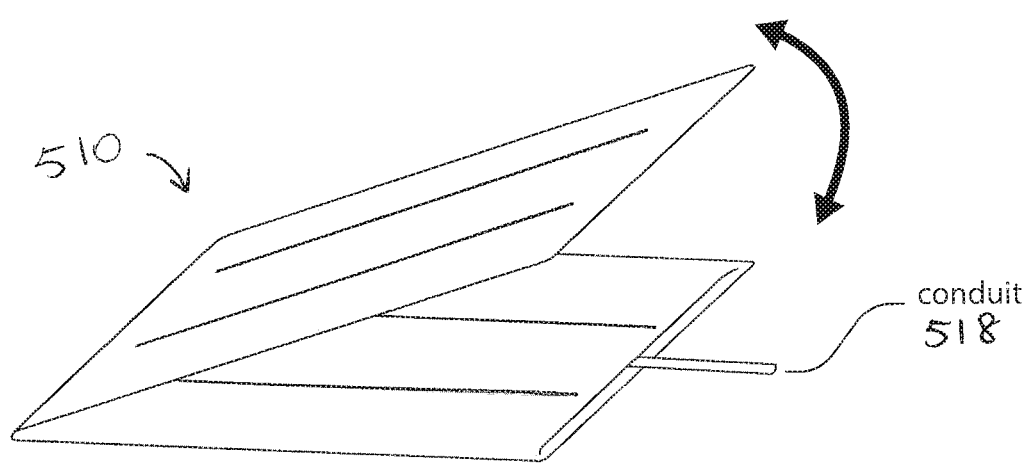
FIG. 18 illustrates an example embodiment of a foldable bladder assembly.

Referring now to FIG. 18, which illustrates an example embodiment of a foldable bladder assembly 510. Bladder assembly 510 can be folded for better packing and portability when the rigid or semi-rigid ribs or segments in the bladder assembly or sleeve assembly comprise multiple sections. As shown, bladder assembly 510 may be folded to reduce a footprint, e.g. an area of space in which bladder assembly occupies.

FIGS. 19A to 19D illustrate a top view and a side view of another example bladder assembly 510 with support beams in a semi-deflated and an inflated state. Inflatable bladder 516 may be positioned adjacent or within sleeve assembly 517. Sleeve support beams 910 may be used to couple bladder 516 on one end and sleeve assembly 517 on the other end, as shown. Sleeve support beams 910 may be coupled to sleeve assembly 517 by hinges 920. Sleeve support beams 910 may be coupled to bladder 516 by bladder support beams 915, hinges 910 or both. When inflated, bladder 516 may push bladder support beams 915 and sleeve support beams 910 on each side to enhance structural integrity and increase tension of the bladder assembly.

Figure 20A:
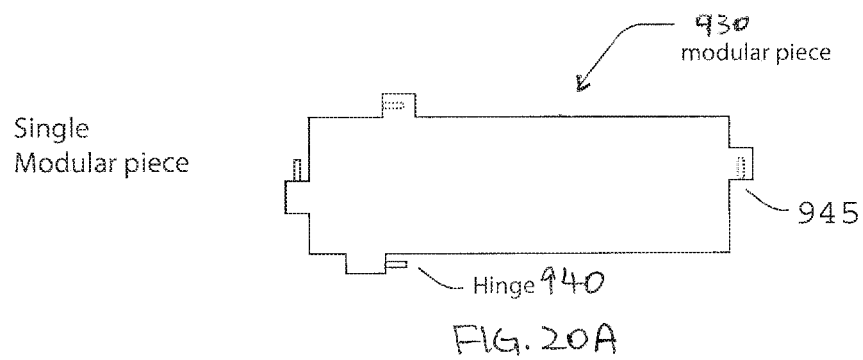
FIG. 20A is a schematic illustration of an example modular piece of an example bladder assembly.
Figure 20B:
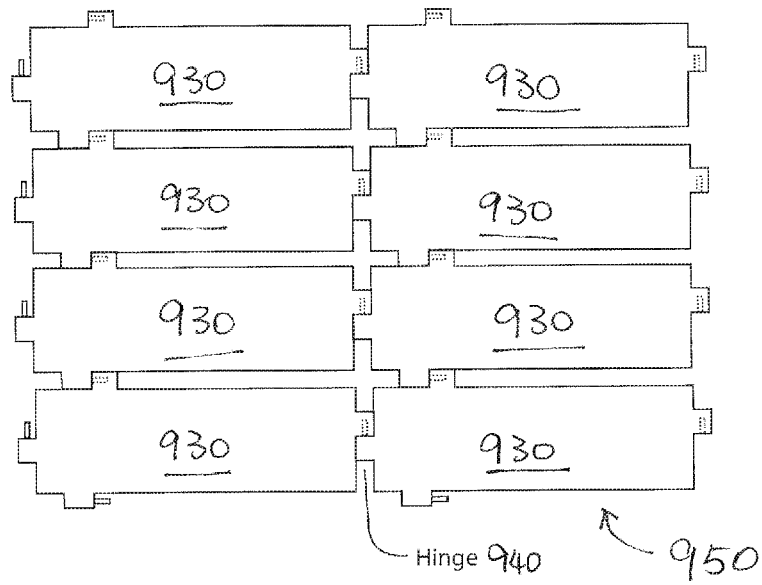
FIG. 20B is a schematic illustration of an example bladder assembly composed of a plurality of modular pieces in FIG. 20A.

FIG. 20A illustrates an example modular piece of an example bladder assembly and FIG. 20B illustrates an example bladder assembly 950 comprising a plurality of modular pieces 930 in FIG. 20A. Each modular piece 930 may comprise one or more hinges 940 and one or more hinge slots 945. A hinge slot 945 from a first modular piece 930 may be configured to receive a hinge 940 from a second modular piece 930, as can be seen in FIG. 20B. Modular pieces 930 may be operable to snap together to form a flat structure that forms body of bladder assembly 950. As hinges 940 may be configured to freely rotate within a hinge slot 945 when connected, bladder assembly 950 may be folded as shown in FIG. 21.

Figure 21:
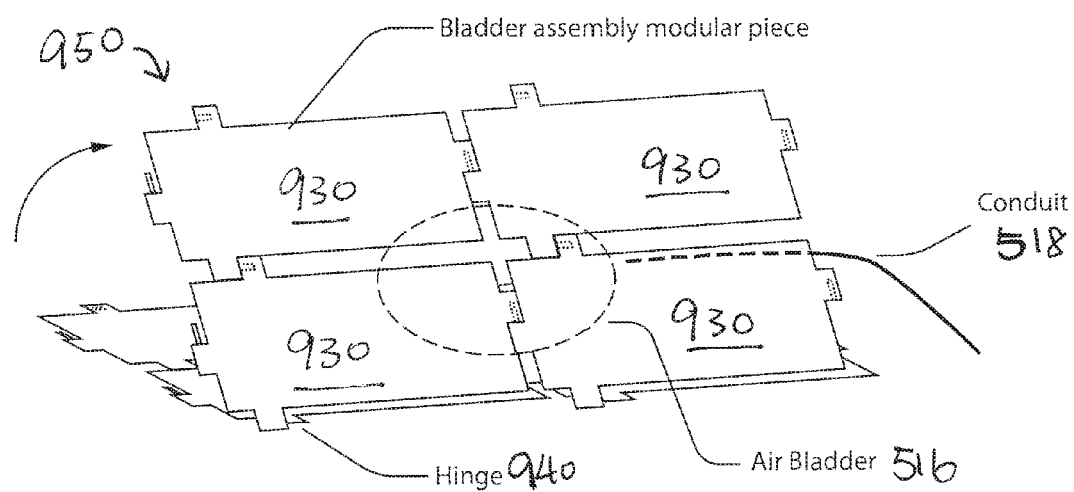
FIG. 21 illustrates a perspective view of a foldable bladder assembly composed of a plurality of modular pieces.

FIG. 21 illustrates a perspective view of a foldable bladder assembly 950 composed of a plurality of modular pieces 930 with an inflatable bladder 516 within the bladder assembly 950.

In some embodiments, hinges 940 of bladder assembly 950 may be configured to only fold in one direction, enabling bladder assembly 950 to raise the user's head vertically, while they can freely fold in the opposite direction.

Figure 22:
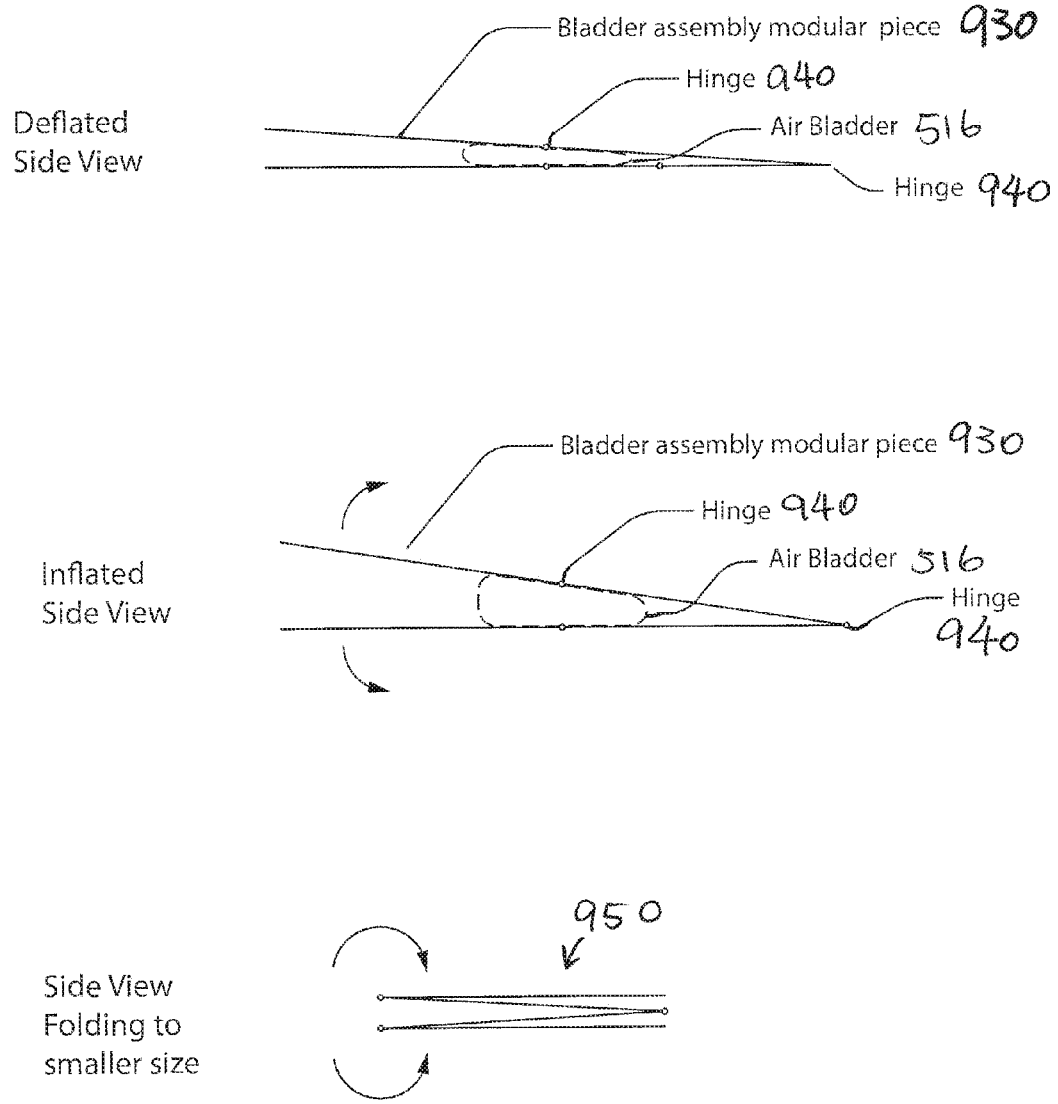
FIG. 22 illustrates various schematic side views of a foldable bladder assembly composed of a plurality of modular pieces.

FIG. 22 illustrates various side views of a foldable bladder assembly composed of a plurality of modular pieces. As shown, inflatable bladder 516 may be connected to two modular pieces 930 by way of hinges 920, 940. The two modular pieces 930 may be connected on one end by a hinge 940 and may be open on the other end (the "open end"). As bladder 516 is inflated, modular pieces 930 coupled to bladder 516 such that the open end of the modular pieces 930 increase in distance, thereby lifting a user's head upward.

In some embodiments, bladder assembly 950 may be folded to a near flat structure comprising a stack of modular pieces 930, as seen in FIG. 22.

Figure 23:
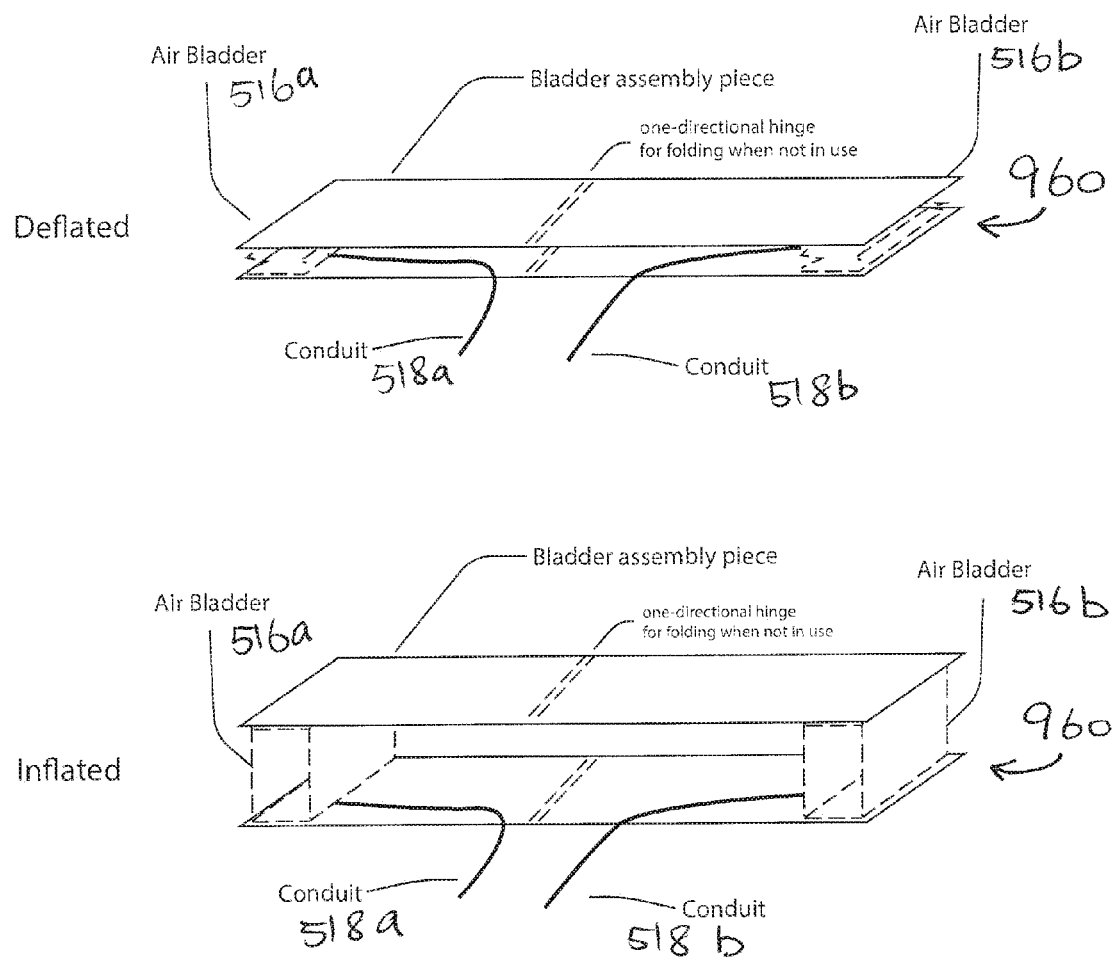
FIG. 23 is a schematic illustration of a bladder assembly with two inflatable bladders.

FIG. 23 illustrates another example bladder assembly with two inflatable bladders 960. Two separate inflatable bladders 516a, 516b each connected to an independent source of air pressure via conduit 518a, 518b respectively. Bladder assembly 960 may include two bladder assembly pieces, for example, a top bladder assembly piece and a bottom assembly piece. Each bladder assembly piece may folded in one direction, such as through a one-direction hinge as shown. As bladders 516a, 516b are inflated, top bladder assembly piece may be moved upwards relative to the bladder bottom assembly piece, thereby raising a user's head.

In some embodiments, bladder assembly 110 may be configured to expand such that all components, including the segments 410, the internal inflatable chamber 420, the hinges or flexible components 415 and the optional external chamber 430 of the bladder assembly, are displaced during the inflation.

For example, all or some components of bladder assembly 110 may be configured to rise at the same rate along a vertical axis of the bladder assembly during the inflation. For example, an entire surface of a top surface of bladder assembly 110 may be configured to rise at the same rate along a vertical axis of the bladder assembly during the inflation. For another example, an entire surface of a top surface of bladder assembly 110 may be configured to rise simultaneously along a vertical axis of the bladder assembly during the inflation.

In some embodiments, bladder assembly 110 may create movement simultaneously along an entire length of the bladder assembly, such that a user's head may be raised in a steady and smooth manner, interrupting or reducing noise from the snoring with minimal disturbance to the user In some embodiments, bladder assembly 110 may include one or more inflatable bladders.

FIG. 5 is an example schematic diagram of another apparatus 50 for snore disruption, according to some embodiments. Apparatus 50 may include a bladder assembly 510, an air inflator 512, a conduit 518, and control unit 514. Apparatus 50 may further include a wired or wireless audio-sensor and transceiver 515, or a mobile device or any other device that would allow for audio sensing and analog or digital transmission. Bladder assembly 510 may be placed underneath a pillow or inside a pillowcase. Bladder assembly 510 may be inflated and deflated by air inflator 512 and through expanding and increasing in volume, and deflating and reducing in volume, gently moving the user's head stimulating throat muscles to open up the airway, hence disrupting the snoring. The bladder assembly 510 may include at least one inflatable bladder 516 placed within a sleeve assembly 517, where the expansion and volume increase of the at least one bladder 516 expands the sleeve assembly 517 as well and extends and transfers the expansion through the length of the entire structure of sleeve assembly 517, therefore displacing the pillow along the length of sleeve assembly 517.

Thus, bladder assembly 510 may longitudinally extend to allow for effective displacement along the length of a pillow used in conjunction with the apparatus.

In some embodiments, no mechanical or electrical components are placed in the pillow or under the head of the user, where bladder assembly 510 is the only component that is placed in close proximity to the user, drastically reducing the issues of any noise and electromagnetic field exposure, allowing for a sleep with minimal disturbance for both user and if applicable, user's partner in the same room.

In some embodiments, apparatus 50 may include a bladder assembly 510, an air inflator 512, a valve 513, a control unit or electronic circuit 514, and a wired or wireless audio-sensor and transceiver 515, which can be wired or wireless microphone transceiver or a cellphone or any other device suitable for audio sensing and analog or digital transmission. The bladder assembly 510 may include at least one inflatable bladder 516 positioned inside a sleeve assembly 517 with a hard or rigid surface. The bladder assembly 510 can also be any other assembly of components that would allow for increase in volume when inflated and reduction of volume when deflated. The bladder 516 is further connected to the inflator 512 through at least one conduit or tube 518. Bladder assembly 510 may be placed underneath a pillow or inside the pillowcase. The inflatable bladder 516 may be inflated and deflated by the inflator 512 and through expanding and increasing in volume and deflating and reducing in volume changes the position of user's head, hence disrupting the snoring.

In some embodiments, bladder assembly 510 may contain no rigid or semi segments.

For example, bladder assembly 510 may contain one or more relatively inflatable bladders 516 without any rigid components. In effect, a combination of multiple bladders that expand during inflation, at all or substantially all parts, simultaneously due to a structural design of the soft fabric or bladder assembly itself may create a tension that may be sufficient to support and raise a user's head a higher position.

In some embodiments, bladder assembly 510 or inflatable bladder 516 may be foldable longitudinally in one or more place so that the bladder assembly 510 or inflatable bladder 516 can be folded into a smaller size and packed for convenience. This foldable configuration may be achieved by using rigid blades to section bladder assembly 510 or inflatable bladder 516 into multiple smaller sections.

Air inflator 512 may pressurize the bladder 516 through at least one tube or conduit 518, which may be a flexible plastic tube. The design of the air inflator 512 may be diaphragm, piston cylinder, blower, or any other suitable means. Air inflator 512 may be covered by soundproof material to reduce any noise when it is on.

Air inflator 512 may be connected to an optional valve 13, which may connect the outlet of inflator 512 to the atmosphere to depressurize the inflated bladder 516 while the inflator 512 is turned off. Valve 513 may be a normally open mini solenoid valve or other suitable valve. For example, valve (or solenoid valve) 513 may be an on/off valve that creates a closed chamber when it is on so that the bladder can fill up. The valve 513 may be opened to allow the bladder 516 to deflate.

In some embodiments, apparatus 50 may further include an optional pressure release valve 523 to prevent the inflatable bladder 516 from bursting or otherwise being damaged from being expanded beyond a certain threshold. The pressure release valve 523 may prevent the bladder 516 from going over a certain pressure threshold.

Air inflator 512 may further be connected to at least one silencing component or silencer 519, which is connected to the outlet of the inflator 512 to reduce the transfer of the noise and vibration to bladder assembly 510.

Control unit 514 may include a power supply 520, which can be a battery or an AC wall outlet or any other suitable sources of electrical power, a sound receiver and processor 521, and a controller 522. The control unit 514 may turn the air inflator 512 on and off and controls the function of the snore disrupting apparatus. The control unit 514 may further comprise an adjustable on and off timer relay, as part of its control system, for setting the period of running the air inflator 512. The control unit 514 can be in part or whole a mobile device or any other suitable device which can allow for sound processing and transmitting.

Sound receiver and processor 521 of the electronic circuit unit 514, receives what electronic signals representing sound waves from the audio-sensor and transceiver 515. The controller 522 of the control unit 514 then turns on the inflator 512 once a snoring sound has been detected. The sound receiver and processor 521 may comprise a noise filter to eliminate the noise and may further comprise a voice recognizing memory or a voice detector to distinguishing an individual snorer's voice. The voice recognizing memory may be utilized when more than one person snores in the same room and separate snore disrupting system are used in close proximity. In this case, the apparatus would recognize the individual user's snoring sound. The snore disrupting system may work with or without voice recognizing memory.

Sound waves may be transmitted by wired or wireless audio-sensor and transceiver 515 or any other device that would allow for audio transmission, to the control unit 514, which switches on the inflator 512 and closes the valve 513, resulting in the inflation of the bladder 516 and thus bladder assembly 510.

What might be a snoring sound may be detected by a wired or wireless audio-sensor and transceiver 515 or any other device suitable for audio transmission, and is transmitted to the sound receiver and processor unit 521 that is in communication with the control system 522. When signaled by the sound receiver and processor unit 521, the control system 522 turns on the inflator 512 and closes the valve 513 for a predefined period of time, and then turns off the inflator 512 and opens the valve 513 for a predefined period of time. The total of the on and off time periods of the inflator 512 make one time cycle of the system. The running on and off of the inflator 512 may be done by a timer relay as part of the control system 522, receiving electrical signals from the sound receiver and processor unit 521.

By turning on the inflator 512, the bladder 516 is inflated, expanding the bladder assembly 510, causing the snorer's head that is located on the pillow or the bladder assembly to gently move up or in any other direction depending on the position of the head during a predefined period of time. After the predefined period of the inflator 12 being on and the bladder assembly 510 reaching a predefined maximum expansion, the inflator 12 is turned off by the control system 522, allowing the bladder 16 to depressurize through the valve 13, causing the bladder assembly 510 to reduce in cross sectional area, resulting in the user's head to move down or in any other direction depending on the position of the head.

In another embodiment, apparatus 50 does not require the audio-sensor and transceiver 515 nor the sound receiver and processor 521 as part of the control unit 514. In this embodiment the control unit 514 may be set to periodically turn the inflator 512 on and off, independent of the snoring sound. The control unit 514 may comprise an adjustable on and off timer relay for setting the period of running the inflator 512. By setting the timer for the period less than the gaps between when the device disrupts the snoring and when the snoring starts again, the user's head may be periodically raised to reduce or eliminate snoring.

FIGS. 6A and 6B show a schematic view illustrating an example embodiment of a sleeve assembly in an inflated position.

In some embodiments, bladder assembly 510 may include a sleeve assembly 517 and an inflatable bladder 516 configured to be received within sleeve assembly 517.

In some embodiments, sleeve assembly 516 may serve as a pillow, or be used with a pillow.

In some embodiments, sleeve assembly 517 may include a plurality of rigid or semi-rigid segments 534, each segment being pivotally hinged to an adjacent segment at each end of the segment, such that inflatable bladder 516, during the inflation, is configured to expand the plurality of rigid or semi-rigid segments 534 outwardly.

In some embodiments, the plurality of rigid or semi-rigid segments 534 are configured to form a cylindrical or polygonal shape.

In some embodiments, each segment 534 may be pivotally hinged to an adjacent segment at a flexible component.

In some embodiments, the flexible component comprises extruded flexible material. In some embodiment, the flexible components may be a relatively thin and soft component compared to rigid or semi-rigid segments 534. Segments 534 and flexible components may be integrally formed or extruded.

In some embodiments, sleeve assembly 517 may include a plurality of flexible pockets or sacs 535, each pocket 535 being configured to receive a corresponding one of the plurality of rigid or semi-rigid segments 534 within, each of the pockets 535 being hinged to adjacent pockets 535 for pivotal movement during the inflation.

The pockets 535 may provide additional comfort for a user as his or her head is rested against bladder assembly 510.

In some embodiments, the rigid or semi-rigid segment 534 may include an elongated bar structure adapted to be received within the corresponding flexible pocket 535.

In some embodiments, sleeve assembly 517 may comprise a flexible sleeve structure 533 and a plurality of flat bars 534 or any other semi-rigid longitudinal structure. The flexible sleeve structure 533 may be made of flexible plastic or robust fabric with parallel longitudinal sacs 535. The flat bars 534 may be made of light and hard material and may be separated in two or many segments. By inserting one flat bar in each sac 535 of the flexible sleeve structure 533, sleeve assembly 517 may form into a reinforced body. By inflating the bladder 516 placed inside sleeve assembly 517, sleeve assembly 517 may form a rigid cylindrical or polygonal shape sleeve, extending and longitudinally transferring the expansion motion of the inflatable bladder 516, thereby pushing up the pillow to change the position of the user's head.

For example, bladder assembly 510 may rise simultaneously alongside an entire length of a pillow if it is being used with a pillow by a user.

FIGS. 7A and 7B show a schematic view illustrating an example embodiment of a sleeve assembly in a deflated position. Illustrated sleeve assembly 517 is shown in a position when the bladder 516 (not shown) has been deflated, resulting in sleeve assembly 517 to fold and reduce in cross-sectional area, thereby causing the user's head to move down and back to the initial position.

Figure 26A:
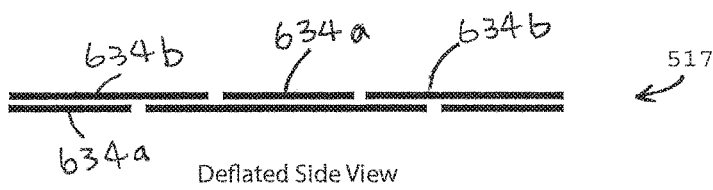
FIG. 26A illustrates a schematic side view of another example sleeve assembly when deflated.
Figure 26B:
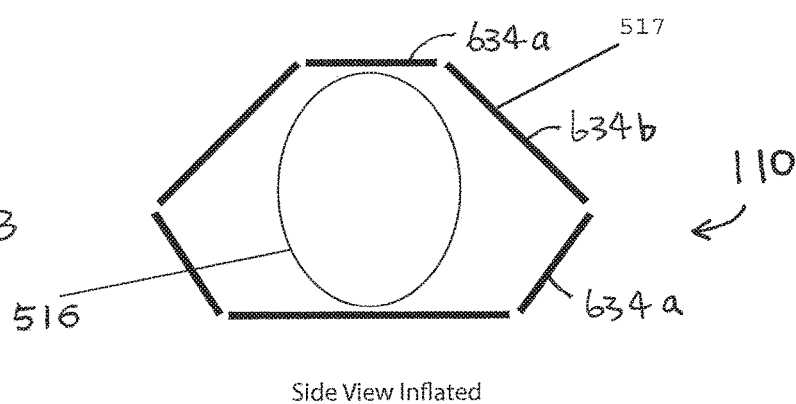
FIG. 26B illustrates a schematic cross-sectional side view of an example inflated bladder assembly with the example sleeve assembly in FIG. 26A.
Figure 26C:
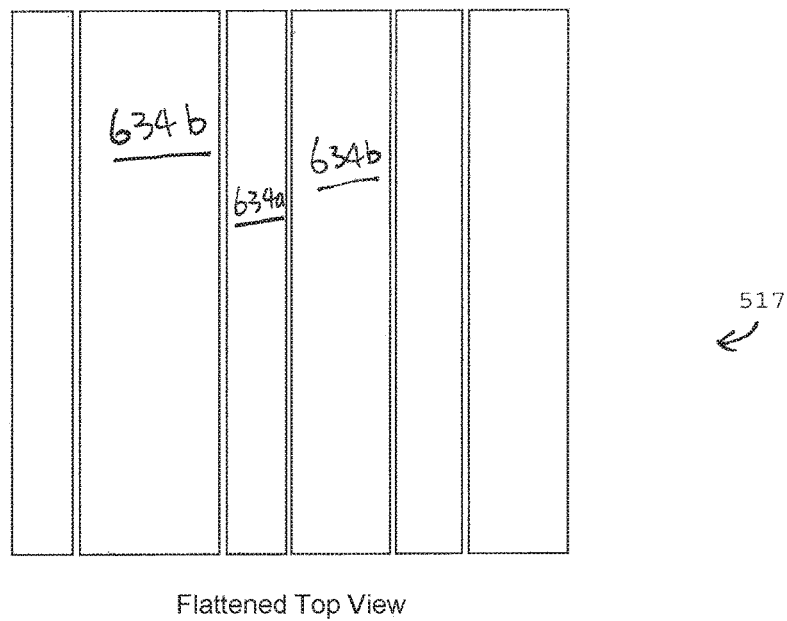
FIG. 26C illustrates a schematic top view of the example sleeve assembly in FIG. 26A when flattened.

Referring now to FIGS. 26A and 26C, which illustrate a schematic side and top view, respectively, of another example sleeve assembly 517 when deflated and flattened. In this example embodiment, sleeve assembly 517 may include a plurality of rigid or semi-rigid segments (e.g. bars) 634a, 634b. In some embodiment, each segment 634a, 634b may be pivotally hinged to an adjacent segment 634a, 634b at each end of the segment 634a, 634b, such that inflatable bladder 516, during inflation, is configured to expand the plurality of rigid or semi-rigid segments 634 outwardly, as shown in FIG. 26B.

The plurality of segments 634 may have varying widths. For example, segments 634a may have a shorter width than segments 634b. This way, the plurality of segments 634a, 634b are configured to form an irregular polygonal shape when expanded.

When expanded by an inflated bladder 516 (see FIG. 26B), the sleeve assembly 517 may have a segment 634b, which has a greater width than that of its adjacent segments 634a, positioned at the bottom of the bladder assembly 110, where a user's head may be positioned on or near the top of the bladder assembly 110 across from the bottom. As can be seen, the width of the segment 634b positioned at the bottom has a sufficient dimension to cover and support a corresponding width of a bottom surface of the inflated bladder 516. The corresponding width of the bottom surface of the inflated bladder 516 may be, in some cases, the entire width of the bottom surface of the bladder 516. This configuration may provide greater stability, such as stationary stability, during the process of inflation or deflation, and when the bladder assembly 110 is inflated for use.

In some cases, this embodiment may limit the foldability of the sleeve assembly 517 in one direction, which may reduce material fatigue and prolong the durability of both bladder and sleeve assemblies.

Even though only segments 634a, 634b with two varying widths have been illustrated in FIGS. 26A to 26C, it is to be appreciated that sleeve assembly 517 may include segments with at least three varying widths.

In some embodiments, each segment 634a, 634b may be pivotally hinged to an adjacent segment at a flexible component (not shown). For example, as illustrated in FIG. 26B, each segment 634a, 634b may be pivotally hinged to adjacent segments 634b, 634a.

The flexible component may be made from extruded flexible material. In some embodiment, the flexible components may be a relatively thin and soft component compared to rigid or semi-rigid segments 634a, 634b. Segments 634a, 634b and flexible components may be integrally formed or extruded.

Figure 8A:
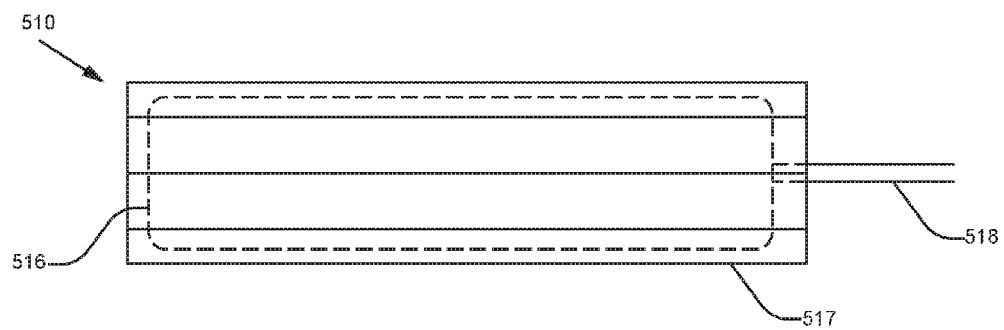
FIG. 8A shows a schematic view illustrating an example embodiment of a bladder assembly.
Figure 8B:
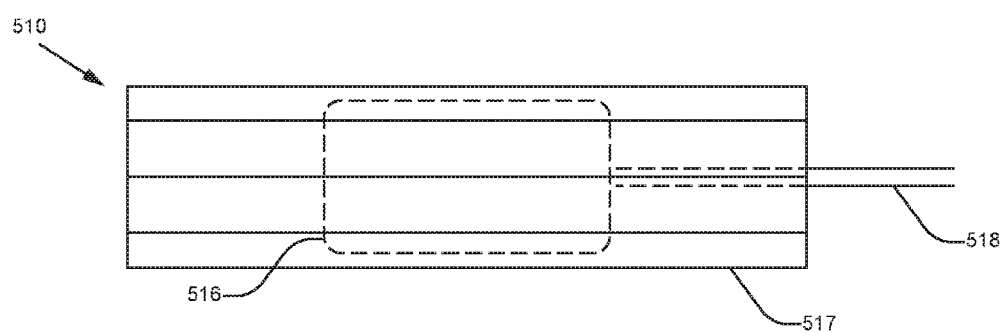
FIG. 8B shows a schematic view illustrating an example embodiment of another bladder assembly.

FIGS. 8A and 8B illustrate various sizes of an inflatable bladder 516 compared to a sleeve assembly 517 in some embodiments. As size of the inflatable bladder 516 becomes smaller, speed of inflation to a pre-determined pressure increases, a smaller bladder 516 (FIG. 8B) would require less air flow to achieve the same height as a bigger bladder 516 (FIG. 8A). Assuming a constant rate of air inflation, a smaller bladder 516 (FIG. 8B) would also require less time to achieve the same height as a bigger bladder 516 (FIG. 8A) during one cycle.

Figure 10:
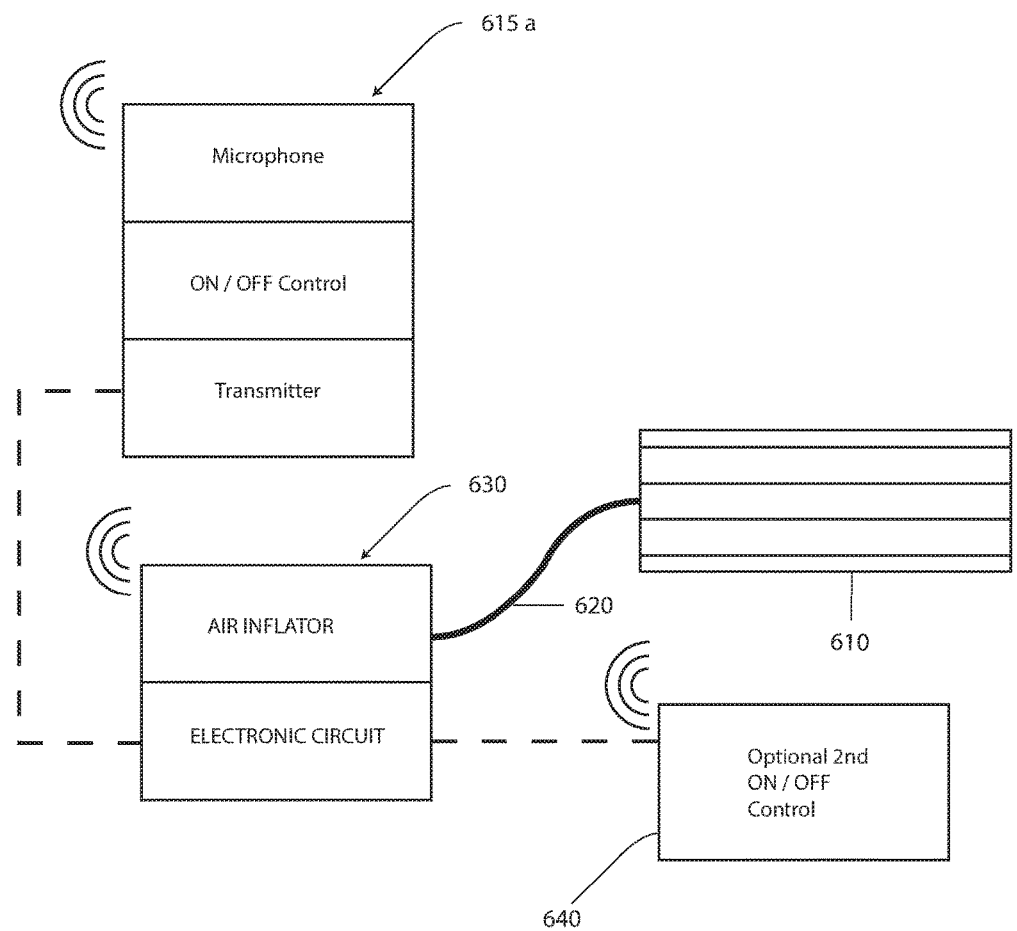
FIG. 10 is an example schematic diagram of an apparatus for snore disruption or prevention for one user with a partner control device.

FIG. 10 is an example diagram of an apparatus for snore disruption for one user with an optional control device. As shown, a housing 630 may include air inflator 140 and other electronics, including for example one or more of controller 130 and audio processor 150. A conduit 620 may extend from air inflator 140 within housing 630, the conduit 620 coupling to a bladder assembly 610. An audio processor or microphone 615, which can also function as an ON/OFF switch and include a transceiver, may be in wireless communication with a controller 130 within housing 630 to transmit sound waves and other electronic signals. An additional ON/OFF switch 640 may be provided to allow a user's partner to switch the apparatus on or off.

Figure 11:
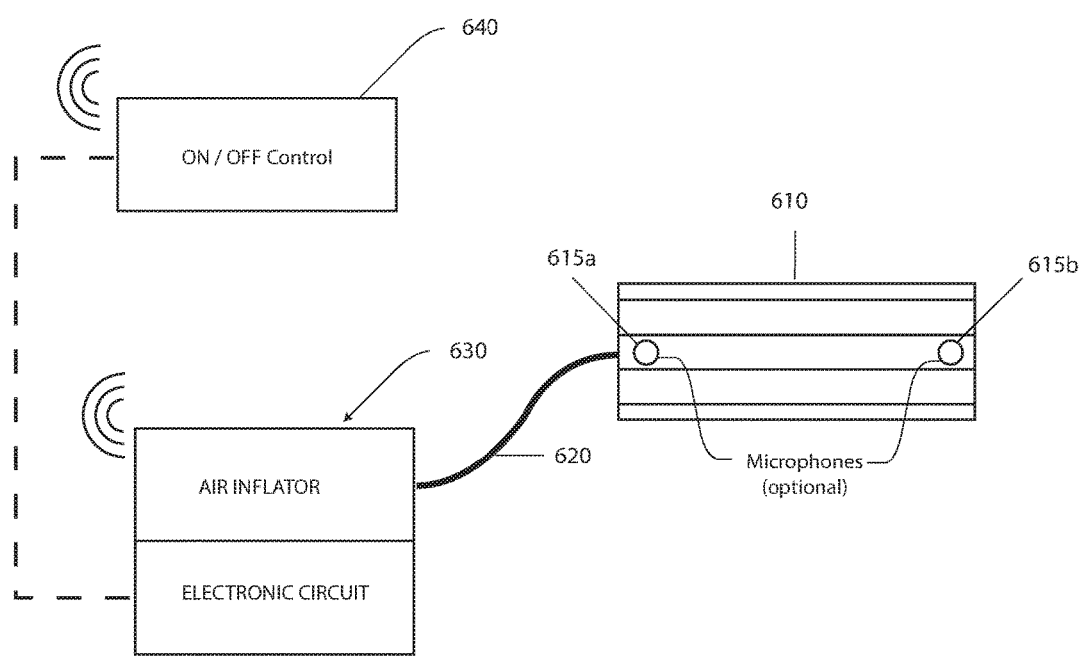
FIG. 11 is an example schematic diagram of an apparatus for snore disruption or prevention with two microphones.

FIG. 11 is an example diagram of an apparatus for snore disruption with two audio sensors or microphones on bladder assembly 610. As shown, a housing 630 may include air inflator 140 and other electronics, including for example one or more of controller 130 and audio processor 150. The microphones 615a, 615b may be configured to discern the location of a snoring sound if multiple sleepers are snoring. Each of the two microphones 615a, 615b may be placed close to a respective end of bladder assembly 610 so that sound waves from a particular source (e.g. an user) adjacent to one microphone 615a may be more easily captured or discerned. For example, a sound wave may be filtered and recognized to be from a particular user as compared to sound waves from a different source (e.g. user's partner sleeping next to user) closer to second microphone 615b. An audio processor 150 or controller 130 may be configured to discern the source of any sound wave coming from a particular microphone, in accordance with methods described herein.

For example, a user may be facing one microphone 615a as opposed to the other microphone 615b, so having two microphones 615a, 615b placed strategically on bladder assembly 610 may facilitate better recording of sound waves coming from a user. For another example, if the user's partner is also sleeping next to the user and is a source of sound waves (e.g. snores or sleep-talking), two microphones can also help with discerning the user's snoring sound, through for instance a triangulation of sound wave signals.

For example, the audio processor may be configured to filter the sound waves to discern a snoring sound of the user from one or more snoring sounds of one or more people other than the user.

Each of microphones 615a, 615b may be connected to or including a transceiver for transmitting sound waves to components housed within housing 630. An ON/OFF switch 640 may be provided for easy and convenient user control.

Figure 12:
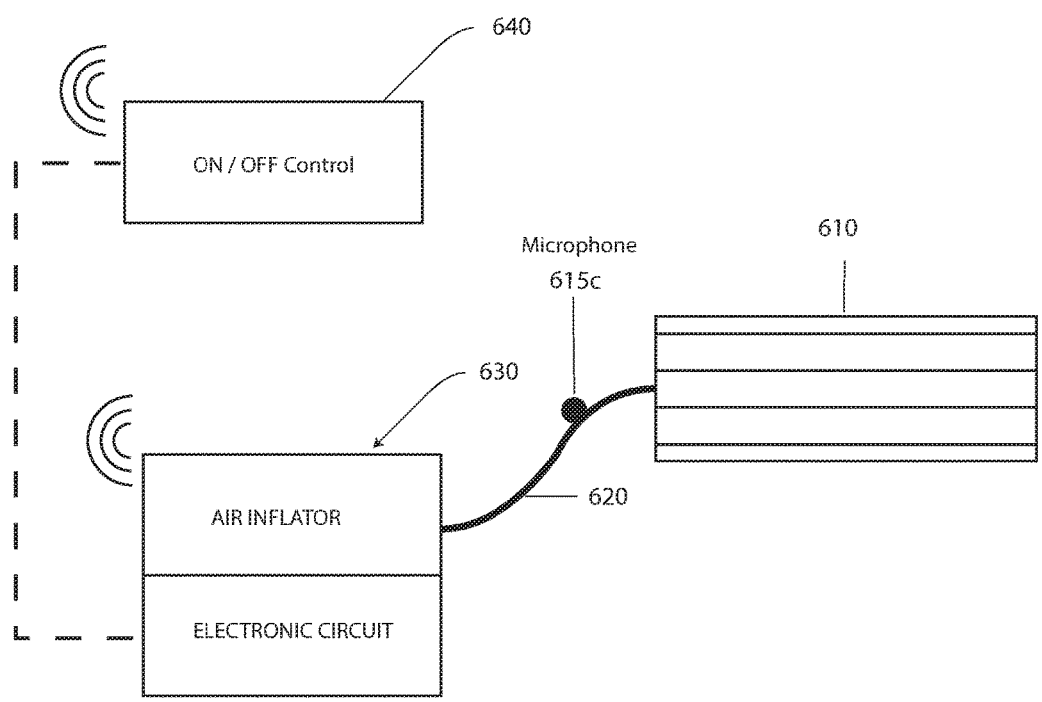
FIG. 12 is another example schematic diagram of an apparatus for snore disruption or prevention.

FIG. 12 is another example diagram of an apparatus for snore disruption or prevention. In this embodiment, a microphone 615 may be placed on conduit 620 as opposed to bladder assembly 610. Microphone 615 may be connected to components in housing 630 either through wire or wirelessly for transmission of sound wave signals.

FIG. 13 is another example diagram of an apparatus for snore disruption with two microphones. Compared to embodiment shown in FIG. 11, in addition to one or more of controller 130 and audio processor 150, housing 630 may also include components such as ON/OFF switch, optional microphone, and may further include other decorative elements such as light source, clock display, radio, and so on.

As shown, all electronic or noisy components such as air inflator 140, electronic circuits, on/off control, on/off control, and optional decorative components such as light, clock, radio and so son may be housed in a housing 630 and placed relatively close to the user, if a pre-determined minimal level of noise, radiation, and electromagnetic field reaches the user from housing 630 while the apparatus is on.

Figure 14:
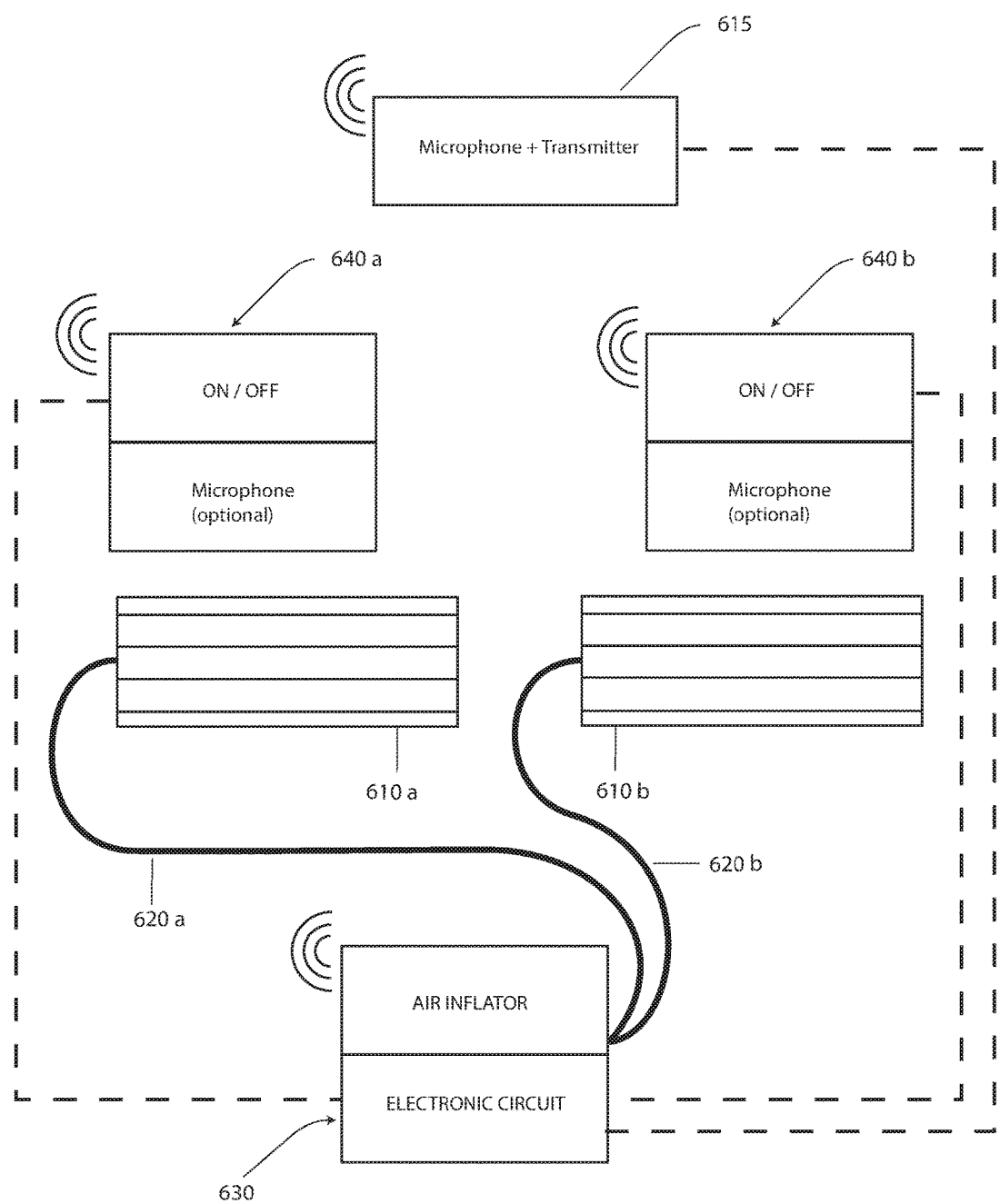
FIG. 14 is an example schematic diagram of an apparatus for snore disruption or prevention for two users.

FIG. 14 is an example diagram of an apparatus for snore disruption for two users. As shown, a housing 630 may include one or more air inflators 140 and other electronics. Two or more conduits 620a, 620b may extend from air inflator 140 within housing 630, each conduit 620a, 620b coupling to a respective bladder assembly 610a, 610b. An audio processor or microphone 615 including a transceiver may be in wireless communication with a controller 130 or audio processor 150 within housing 630 to transmit sound waves and other electronic signals. One or more ON/OFF switches 640a, 640b may be provided, each configured to control a respective bladder assembly 610a, 610b or the entire apparatus.

In some embodiments, ON/OFF switches 640a, 640b may optionally include a microphone. Audio processor 150 may be coupled to a plurality of audio sensors or microphones 615, 640a, 640b and configured to receive sound waves from the plurality of sources as detected by the one or more microphones 615, 640a, 640b, and audio processor 150 may be configured to identify a location of a snorer by analyzing the sound waves from the plurality of sources 615, 640a, 640b. For example, analyzing the sound waves may include triangulation of sound waves coming from the plurality of microphones 615, 640a, 640b.

Figure 15:
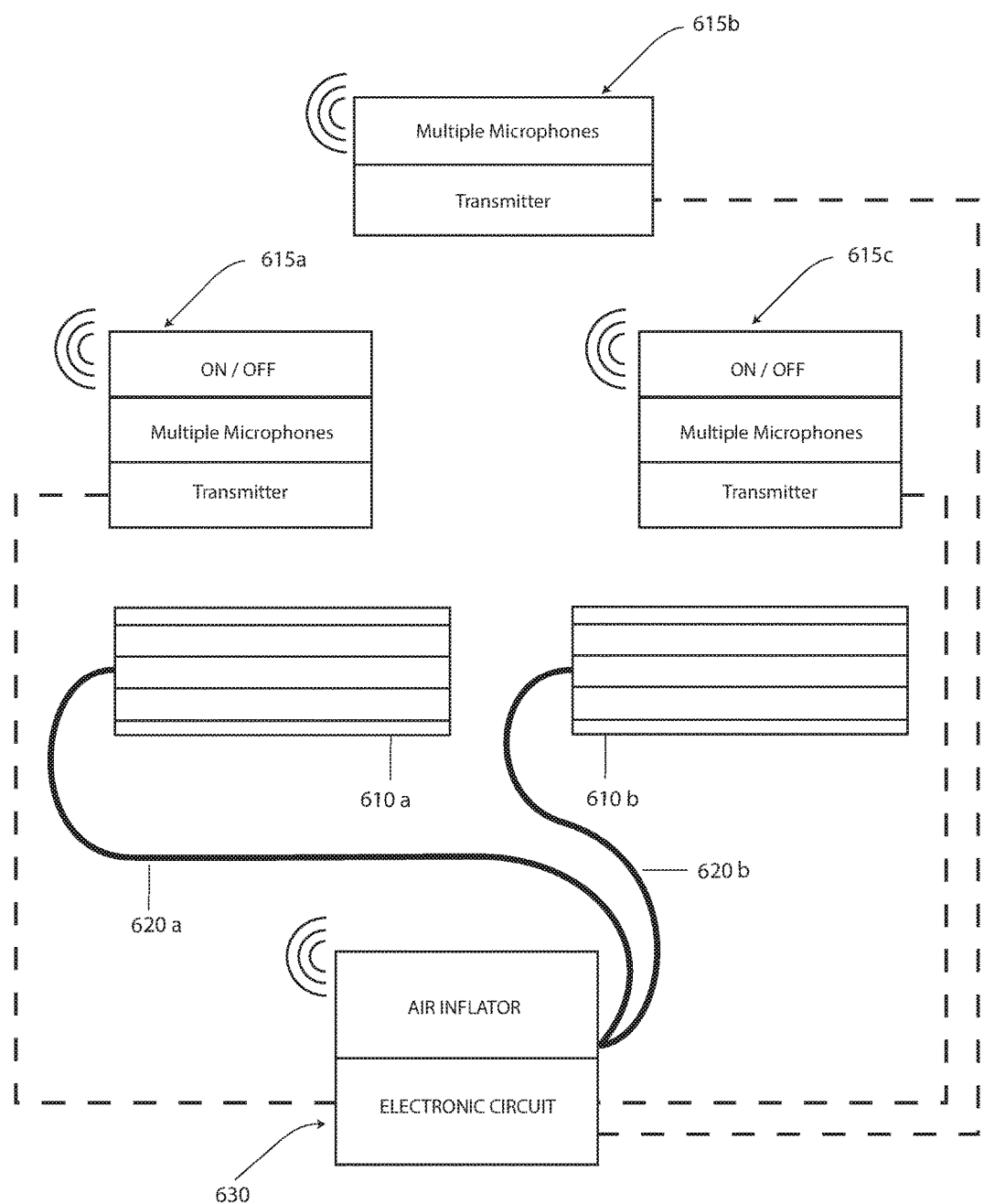
FIG. 15 is another example schematic diagram of an apparatus for snore disruption or prevention for two users.

FIG. 15 is another example diagram of an apparatus for snore disruption for two users. In this embodiment, there may be a plurality of microphones 615a, 615b, 615c, which may be configured to receive sound waves from one or more sources (e.g. users). A control unit may be operable to apply triangulation method in order to discern sources of various sound waves coming from different microphones 615a, 615b, 615c, such that location or pattern of specific sound waves may be determined. For example, a location of a source of a snoring sound may be determined. For another example, a user's snoring sound may be determined based on a user's snoring pattern or any other unique indication, even among a plurality of users snoring at or around the same time. One or more of the microphones 615a, 615b, 615c may also function as an ON/OFF switch or include a transceiver. In some embodiments, each of the device 615a, 615b, 615c may include a plurality microphones, as shown.

Figure 16:
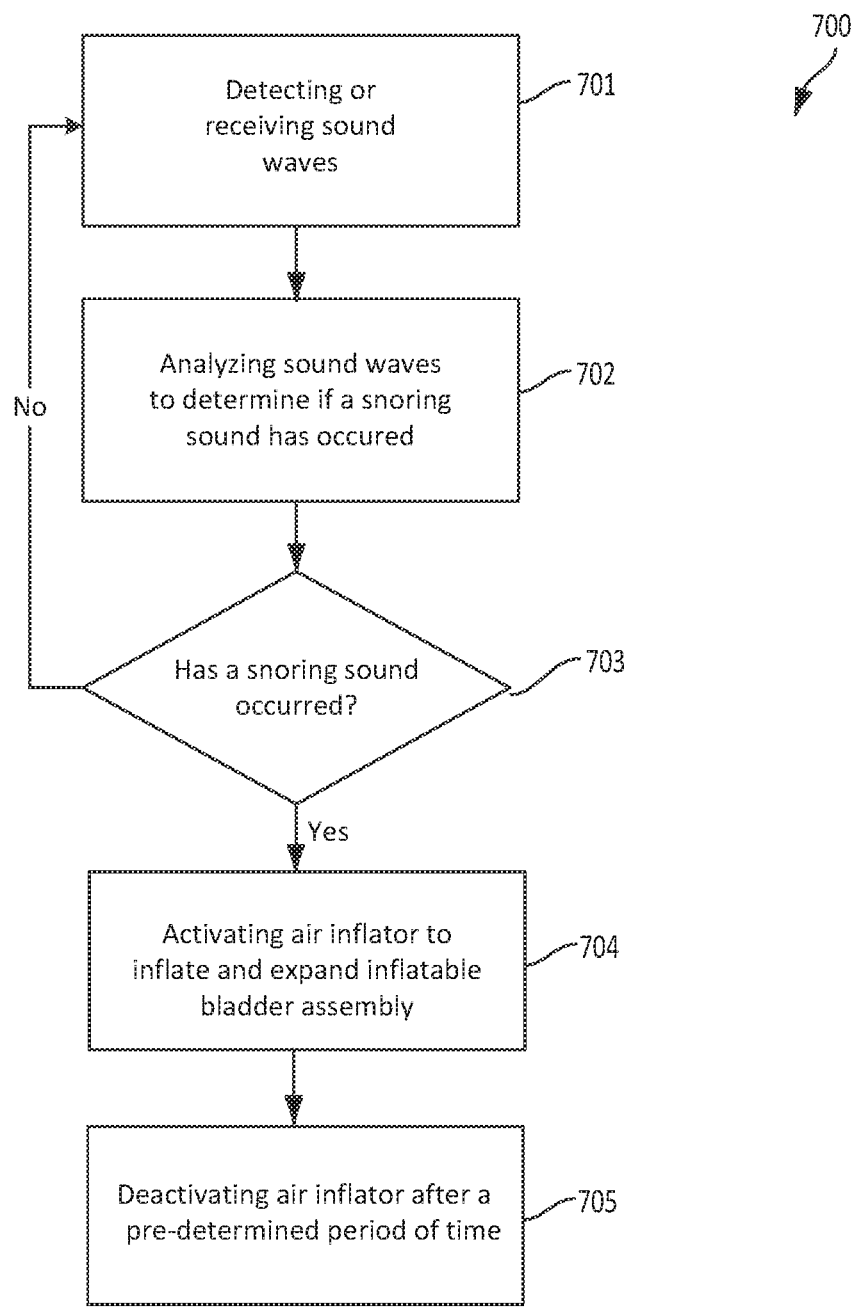
FIG. 16 is a flowchart illustrating a method of snore detection and disruption as performed by an apparatus for snore disruption.

FIG. 16 is a flowchart illustrating a method of snore detection and disruption as performed by an apparatus for snore disruption. The method 700 may include: at step 701, detecting or receiving sound wave by an audio sensing component; at step 702, analyzing, by a controller in communication with the audio sensing component, said sound wave to determine if a snoring sound has occurred; at step 703, upon determining that the snoring sound has occurred: at step 704, activating an air inflator outside of the pillow, by the controller, to inflate and expand an inflatable bladder assembly to cause a pillow to move to a raised position, wherein the bladder assembly is connected to the air inflator through a conduit, the conduit extendable from the bladder assembly at a distance so that the user is not disturbed by any sound of the air inflator being activated; and at step 705, deactivating the air inflator, by the controller, after a predetermined period of time, to lower the pillow from the raised position.

In some embodiments, the method may further include determining, by an audio processor: 1) that the snoring sound has occurred; and 2) an digital snore signature of the snoring sound by processing the sound waves.

In some embodiments, the digital snore signature may include electronic identification data corresponding to a recognized user. The electronic identification data may be, for example, a snoring frequency, a snoring pitch, a sleeping location, or time of snoring through a sleep duration of a certain amount.

User profiles may be stored locally or remotely, for example, at database 220. Each user profile may include a snoring profile and other user information such as name, age, gender, occupation, and so on.

Each snoring profile may include a user's historical snoring pattern data, any relevant medical information, and other electronic information pertaining to the user's snoring habits.

In some embodiments, an audio processor may be configured to recognize a user associated with the sound wave and the snoring sound using stored historical sound waves. The historical sound waves may for example correspond or represent a user's snoring pattern as stored in a user's snoring profile. The historical sound waves may be analyzed to generate a digital snore signature.

In some embodiments, the method 700 may include recognizing and filtering the sound wave to discern the snoring sound from other types of sounds. The method may further include receiving confirmation of the detected snoring sound or an error to refine the audio processor using machine learning. Machine learning may include using user feedback as received from local or remote database to refine the process to filter and recognize the received sound waves. The user feedback may include, for example, user snoring patterns from other users or from the same users. Machine learning can also enhance the overall performance by correlating conditions leading to best results from one user or multiple users.

Figure 17:
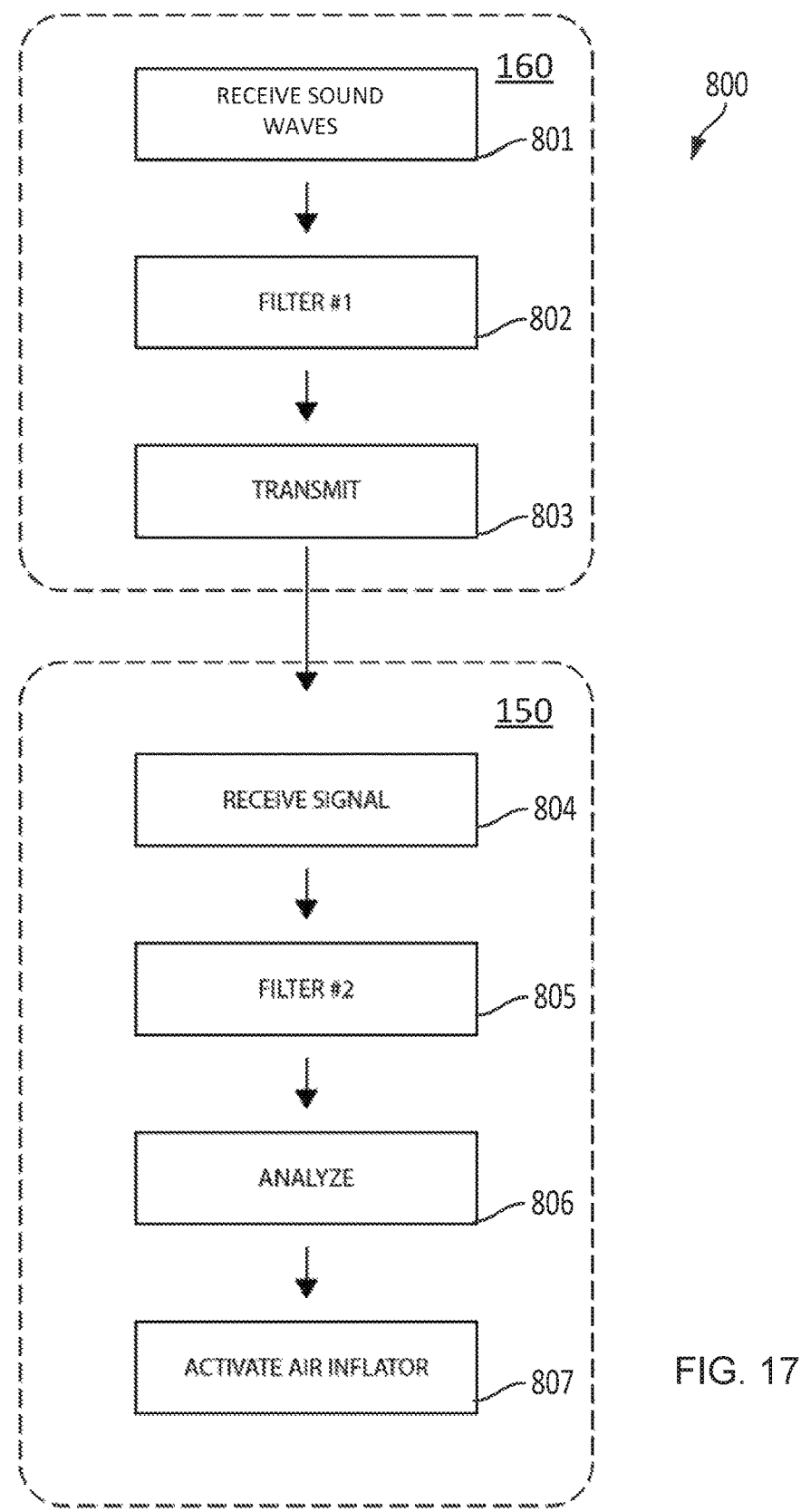
FIG. 17 is a flowchart illustrating a method of discerning a snoring sound.

For example, as seen in FIG. 17, a method of discerning snoring is shown. At step 801, sound waves are received by an audio sensor 160 of apparatus 10, 20, 50; at step 802, a filter is applied to the received sound waves to generate processed sound waves. The filter at step 802 may be a band-pass filter (e.g. combination of high and low filter) to limit transmission to the audio processor 150 to the frequencies relevant or needed for detecting or recognizing snoring. In another embodiment, the filter in step 802 may only filter sounds based on a volume threshold; at step 803, signals representing processed sound waves are transmitted to audio processor 150; at step 804, audio processor 150 may receive the transmitted signals; at step 805, a second filter is applied to the received signals to generate a second set of processed sound waves, the filter in step 805 may be a band-pass filter to narrow the received audio signals to frequencies relevant or needed for detecting snoring; at step 806, the processed sound waves are analyzed to determine if a snoring sound has occurred; if it has, then at step 807, a control signal may be sent to controller 130 to activate the air inflator 140.

In one embodiment, any one of controller 130, audio sensor 160 and audio processor 150 may perform steps 801, 802, 805, 806, 807, eliminating the need for steps 803 and 804. For example, filter in step 802 and filter in step 805 may be combined into one filter.

Referring back to FIG. 16, the method 700 may include correlating the sound waves to additional sound waves received from other devices and stored on a shared or cloud storage device such as database 220. The additional sound waves may be from the same user, or from different users.

In some embodiments, the method 700 may include actuating the inflatable bladder assembly for different lengths of time and different intervals of time based on one or more inflation patterns.

In some embodiments, the method 700 may include: 1) predicting the occurrence of the snoring sound prior to a detection of the snoring sound from the sound waves; and 2) triggering the controller to actuate the inflatable bladder assembly, the prediction based on a snoring profile of a user, the snoring profile comprising at least historical user data.

For example, users may have different snoring profiles with different snoring patterns. A snoring pattern may be, for example, user A typically starts snoring 2 hours from bedtime or a specific time of the day (e.g. 11 PM). Based on user A's snoring pattern, controller 130 or audio processor 150 may predict when a user is likely to start snoring, and activate the air inflator to prevent such snoring prior to the actual occurrence of snoring.

For another example, prediction of snoring may also be based on other users' snoring profile including corresponding snoring patterns. For instance, if user A belongs to a user group that has similar characteristics or attributes, such as any combination of age, gender, ethnicity, weight and so on, then based on historical user data, it may be determined that user A likely has a snoring pattern similar to the average snoring pattern of the users of said user group. Therefore, the apparatus may employ other users' snoring profiles or snoring patterns, as stored locally or remotely, in order to make a prediction as to when user A is likely to snore, or how often user A likely snores during a night. This way, even without user A's personal snoring pattern data, an apparatus may be operable to predict user A's snoring occurrence and activates air inflator to inflate bladder assembly in order to prevent user A's snoring.

The disclosure herein provides many example embodiments of the inventive subject matter. Although each embodiment represents a single combination of inventive elements, the inventive subject matter is considered to include all possible combinations of the disclosed elements. Thus if one embodiment comprises elements A, B, and C, and a second embodiment comprises elements B and D, then the inventive subject matter is also considered to include other remaining combinations of A, B, C, or D, even if not explicitly disclosed.

Some embodiments of the devices, systems and methods described herein may be implemented in a combination of both hardware and software. These embodiments may be implemented on programmable computers, each computer including at least one processor, a data storage system (including volatile memory or non-volatile memory or other data storage elements or a combination thereof), and at least one communication interface.

Program code is applied to input data to perform the functions described herein and to generate output information. The output information is applied to one or more output devices. In some embodiments, the communication interface may be a network communication interface. In embodiments in which elements may be combined, the communication interface may be a software communication interface, such as those for inter-process communication. In still other embodiments, there may be a combination of communication interfaces implemented as hardware, software, and combination thereof.

Numerous references may be made regarding servers, services, interfaces, portals, platforms, or other systems formed from computing devices. It should be appreciated that the use of such terms is deemed to represent one or more computing devices having at least one processor configured to execute software instructions stored on a computer readable tangible, non-transitory medium. For example, a server can include one or more computers operating as a web server, database server, or other type of computer server in a manner to fulfill described roles, responsibilities, or functions.

The term "connected" or "coupled to" may include both direct coupling (in which two elements that are coupled to each other contact each other) and indirect coupling (in which at least one additional element is located between the two elements). "Coupled to" or "coupled with" may include both wired connection or wireless connection.

The technical solution of embodiments may be in the form of a software product. The software product may be stored in a non-volatile or non-transitory storage medium, which can be a compact disk read-only memory (CD-ROM), a USB flash disk, or a removable hard disk. The software product includes a number of instructions that enable a computer device (personal computer, server, or network device) to execute the methods provided by the embodiments.

The embodiments described herein are implemented by physical computer hardware, including in some embodiments computing devices, servers, receivers, transmitters, processors, memory, displays, and networks. The embodiments described herein provide useful physical machines and particularly configured computer hardware arrangements. The embodiments described herein are directed to electronic machines and methods implemented by electronic machines adapted for processing and transforming electromagnetic signals which represent various types of information. The embodiments described herein pervasively and integrally relate to machines, and their uses; and the embodiments described herein have no meaning or practical applicability outside their use with computer hardware, machines, and various hardware components. Substituting the physical hardware particularly configured to implement various acts for non-physical hardware, using mental steps for example, may substantially affect the way the embodiments work. Such computer hardware limitations are clearly essential elements of the embodiments described herein, and they cannot be omitted or substituted for mental means without having a material effect on the operation and structure of the embodiments described herein. The computer hardware is essential to implement the various embodiments described herein and is not merely used to perform steps expeditiously and in an efficient manner.

Although the embodiments have been described in detail, it should be understood that various changes, substitutions and alterations can be made herein without departing from the scope as defined by the appended claims.

Moreover, the scope of the present application is not intended to be limited to the particular embodiments of the process, machine, manufacture, composition of matter, means, methods and steps described in the specification. As one of ordinary skill in the art will readily appreciate from the disclosure, processes, machines, manufacture, compositions of matter, means, methods, or steps, presently existing or later to be developed, that perform substantially the same function or achieve substantially the same result as the corresponding embodiments described herein may be utilized. Accordingly, the appended claims are intended to include within their scope such processes, machines, manufacture, compositions of matter, means, methods, or steps.

As can be understood, the examples described above and illustrated are intended to be exemplary only.

What is claimed here is:

1. An apparatus for disrupting or preventing snoring, the apparatus comprising:
    a bladder assembly comprising:
        a collapsible structure comprising: rigid segments pivotally hinged together, wherein the rigid segments comprise at least a first segment with a first width and a second segment with a second width, wherein the first width is greater than the second width; and
        an inflatable bladder positioned within the collapsible structure;
        wherein the inflatable bladder is configured to be inflated such that an entire top surface of the collapsible structure rises simultaneously along a length of the bladder assembly, and wherein the collapsible structure is configured to support a head of a user during inflation;
    a conduit connecting an air inflator to the inflatable bladder, the air inflator for inflating the inflatable bladder;
    a controller in communication with the air inflator to actuate the air inflator to inflate the inflatable bladder; and
    an audio processor in communication with the controller, the audio processor being configured to detect sound waves and transmit control commands to the controller to trigger actuation of the air inflator upon detection of a trigger event.

2. The apparatus of claim 1, wherein the controller is configured to control a speed at which the air inflator inflates the inflatable bladder within the bladder assembly at a pre-determined inflation rate to provide different inflation patterns.

3. The apparatus of claim 1, wherein the apparatus further comprises an audio sensor or microphone coupled to the audio processor to receive the sound waves.

4. The apparatus of claim 1, wherein collapsible structure comprises a sleeve assembly, the sleeve assembly forms said plurality of rigid segments, each rigid segment being pivotally hinged to an adjacent rigid segment, such that the inflatable bladder, during the inflation, is configured to expand the plurality of rigid segments outwardly along a longitudinal axis of the bladder assembly.

5. The apparatus of claim 4, wherein, when expanded, the plurality of rigid segments are configured to form a cylindrical or polygonal shape.

6. The apparatus of claim 4, wherein the first segment is positioned at a bottom of below the inflatable bladder when the inflatable bladder is inflated.

7. The apparatus of claim 4, wherein each of said rigid segments is pivotally hinged to an adjacent segment at a flexible component.

8. The apparatus of claim 4, wherein the sleeve assembly comprises a plurality of longitudinal pockets, each longitudinal pocket hinged to adjacent longitudinal pockets for pivotal movement during the inflation, each longitudinal pocket configured to receive a corresponding one of the plurality of rigid segments.

9. The apparatus of claim 8, wherein each pocket is further configured to receive two or more of the plurality of rigid segments.

10. The apparatus of claim 1, wherein the controller is configured to actuate the air inflator to inflate the inflatable bladder until a pressure release valve a pre-determined pressure.

11. The apparatus of claim 1, wherein the audio processor couples to one or more audio sensors or microphones and is configured to receive sound waves from a plurality of sources as detected by the one or more audio sensors or microphones, and wherein the audio processor is configured to identify a user by analyzing the sound waves, the user being one of the plurality of sources.

12. The apparatus of claim 1, wherein the audio processor couples to two or more audio sensors or microphones and is configured to receive sound waves from a plurality of sources as detected by the two or more audio sensors or microphones, and wherein the audio processor is configured to identify a location of a user by analyzing the sound waves, the user being one of the plurality of sources.

13. The apparatus of claim 1, wherein the controller activates a cycle when the snore sound is detected to trigger a cycle of inflation and deflation.

14. The apparatus of claim 1, wherein the trigger event comprises at least one of:
    detection of a snore sound;
    identification of a snore sound of a user;
    a prediction of a snore sound; or
    a predefined time period.

15. The apparatus of claim 1, wherein inflation of the inflatable bladder causes the collapsible structure to expand, which transforms the collapsible structure from being structurally flexible to structurally rigid, and changes the height of the collapsible structure uniformly and simultaneously across its length, while the collapsible structure supports a head of a user, regardless of the location of the user's head.

16. The apparatus of claim 1, wherein the inflatable bladder is further configured to deflate such that the entire top surface of the collapsible structure lowers simultaneously along the entire length of the bladder assembly while the collapsible structure supports a head of a user.

17. The apparatus of claim 16, wherein the controller is configured to actuate the air inflator on with an inflating time and subsequently off with a deflating time to provide an inflation cycle initiated once the trigger event is detected.

18. The apparatus of claim 16, wherein the controller is configured to actuate the air inflator on until a pressure control reaches an inflation pressure and subsequently off until the pressure control reaches a deflation pressure to provide an inflation cycle initiated once the trigger event is detected.

19. The apparatus of claim 1, wherein the bladder assembly further comprises one or more additional inflatable bladders positioned within the collapsible structure, and one or more additional corresponding inflators, each of said inflatable bladders connected to one of said corresponding inflators.

20. The apparatus of claim 1, wherein:
the bladder assembly is adapted to be placed under a pillow; and
the air inflator, audio processor, and controller are located at a distance away from the pillow.

21. The apparatus of claim 1, wherein the controller is configured to actuate the air inflator to inflate the inflatable bladder until the bladder assembly reaches a predetermined size.

\* \* \* \* \*